United States Patent
Fuimaono et al.

(10) Patent No.: US 7,410,486 B2
(45) Date of Patent: *Aug. 12, 2008

(54) ABLATION CATHETER HAVING STABILIZING ARRAY

(75) Inventors: Kristine B. Fuimaono, Covina, CA (US); Robert W. Pike, Jr., Coto de Caza, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 11/024,537

(22) Filed: Dec. 29, 2004

(65) Prior Publication Data

US 2005/0113822 A1    May 26, 2005

Related U.S. Application Data

(62) Division of application No. 10/201,052, filed on Jul. 23, 2002, now Pat. No. 6,866,662.

(51) Int. Cl.
*A61B 18/18* (2006.01)

(52) U.S. Cl. .................. 606/41; 607/122; 600/374
(58) Field of Classification Search .............. 606/27, 606/28, 38–42, 45–50; 607/101, 102, 116, 607/122; 600/374, 381
See application file for complete search history.

(56) References Cited

U.S. PATENT DOCUMENTS 4,203,430 A    5/1980    Takahashi
(Continued)

FOREIGN PATENT DOCUMENTS

EP    0 499 491 A2    8/1992
(Continued)

OTHER PUBLICATIONS

M. Haissaguerre et al., Spontaneous Initiation of Atrial Fibrillation by Ectopic Beats Originating in the Pulmonary Veins, The New England Journal of Medicine, 339:659-666 (Sep. 3, 1998).

*Primary Examiner*—Michael Peffley
(74) *Attorney, Agent, or Firm*—Christie, Parker & Hale, LLP.

(57) ABSTRACT

A circumferential ablation catheter is provided, which is particularly useful for treating atrial arrhythmia by ablating a substantial portion of a circumferential region of tissue in a tubular region of or near the heart of a patient. The catheter comprises an elongated tubular catheter body having an outer wall, proximal and distal ends, and at least one lumen extending therethrough. An ablation assembly is mounted at the distal end of the catheter body. The ablation assembly comprises a circumferential ablation element mounted on the distal end of the catheter body, and an inflatable balloon provided in surrounding relation to the circumferential ablation element. The inflatable balloon is adjustable between a radially collapsed position and a radially expanded position. The catheter further comprises a stabilization assembly mounted on the catheter distal to the ablation assembly. The stabilization assembly is designed to contact a plurality of points about an inner circumference of the generally tubular region of or near the heart, and thus serves to stabilize the distal end of the catheter during ablation. The stabilization preferably includes one or more electrodes that can be used for mapping, recording and/or ablating the inner circumference of the generally tubular region of or near the heart.

40 Claims, 12 Drawing Sheets

U.S. PATENT DOCUMENTS

| | | | |
|---|---|---|---|
| 4,207,873 | A | 6/1980 | Kruy |
| 4,777,955 | A | 10/1988 | Brayton et al. |
| 4,882,777 | A | 11/1989 | Narula |
| 4,920,980 | A | 5/1990 | Jackowski |
| 4,960,134 | A | 10/1990 | Webster, Jr. |
| 4,984,581 | A | 1/1991 | Stice |
| 5,170,787 | A | 12/1992 | Lindegren |
| 5,255,679 | A | 10/1993 | Imran |
| 5,263,493 | A | 11/1993 | Avitall |
| 5,275,162 | A | 1/1994 | Edwards et al. |
| 5,304,214 | A | 4/1994 | DeFord et al. |
| 5,327,905 | A | 7/1994 | Avitall |
| 5,354,297 | A | 10/1994 | Avitall |
| 5,383,923 | A | 1/1995 | Webster, Jr. |
| 5,445,148 | A | 8/1995 | Jaraczewski et al. |
| 5,456,664 | A | 10/1995 | Heinzelman et al. |
| 5,487,385 | A | 1/1996 | Avitall |
| 5,540,679 | A | 7/1996 | Fram et al. |
| 5,545,200 | A | 8/1996 | West et al. |
| 5,549,581 | A | 8/1996 | Lurie et al. |
| 5,575,772 | A | 11/1996 | Lennox |
| 5,582,609 | A | 12/1996 | Swanson et al. |
| 5,617,854 | A | 4/1997 | Munsif |
| 5,626,136 | A | 5/1997 | Webster, Jr. |
| 5,642,736 | A | 7/1997 | Avitall |
| 5,656,030 | A | 8/1997 | Hunjan et al. |
| 5,673,695 | A | 10/1997 | McGee et al. |
| 5,680,860 | A | 10/1997 | Imran |
| 5,730,127 | A | 3/1998 | Avitall |
| 5,755,760 | A | 5/1998 | Maguire et al. |
| 5,782,760 | A | 7/1998 | Schaer |
| 5,797,905 | A | 8/1998 | Fleischman et al. |
| 5,800,428 | A | 9/1998 | Nelson et al. |
| 5,823,955 | A | 10/1998 | Kuck et al. |
| 5,827,278 | A | 10/1998 | Webster, Jr. |
| 5,836,947 | A | 11/1998 | Fleischman et al. |
| 5,860,920 | A | 1/1999 | McGee et al. |
| 5,860,974 | A | 1/1999 | Abele |
| 5,865,800 | A | 2/1999 | Mirarchi et al. |
| 5,879,295 | A | 3/1999 | Li et al. |
| 5,882,333 | A | 3/1999 | Schaer et al. |
| 5,882,346 | A | 3/1999 | Pomeranz et al. |
| 5,899,860 | A | 5/1999 | Pfeiffer et al. |
| 5,931,811 | A | 8/1999 | Haissaguerre et al. |
| 5,935,102 | A | 8/1999 | Bowden et al. |
| 5,938,694 | A | 8/1999 | Jaraczewski et al. |
| 5,951,471 | A | 9/1999 | de la Rama et al. |
| 5,984,909 | A | 11/1999 | Lurie et al. |
| 5,997,526 | A | 12/1999 | Giba et al. |
| 6,002,955 | A | 12/1999 | Willems et al. |
| 6,035,224 | A | 3/2000 | West |
| 6,064,902 | A | 5/2000 | Haissaguerre et al. |
| 6,088,614 | A | 7/2000 | Swanson |
| 6,090,104 | A | 7/2000 | Webster, Jr. |
| 6,096,036 | A | 8/2000 | Bowe et al. |
| 6,102,908 | A | 8/2000 | Tu et al. |
| 6,106,522 | A | 8/2000 | Fleischman et al. |
| 6,117,101 | A | 9/2000 | Diederich et al. |
| 6,129,724 | A | 10/2000 | Fleischman et al. |
| 6,146,381 | A | 11/2000 | Bowe et al. |
| 6,162,219 | A | 12/2000 | Nilsson et al. |
| 6,169,916 | B1 | 1/2001 | West |
| 6,171,277 | B1 | 1/2001 | Ponzi |
| 6,219,582 | B1 | 4/2001 | Hofstad et al. |
| 6,242,472 | B1 | 6/2001 | Sekins et al. |
| 6,325,797 | B1 * | 12/2001 | Stewart et al. ................. 606/41 |
| 6,383,151 | B1 * | 5/2002 | Diederich et al. ............... 601/2 |
| 6,529,756 | B1 * | 3/2003 | Phan et al. ................... 600/374 |
| 6,547,788 | B1 | 4/2003 | Maguire et al. |
| 6,645,199 | B1 * | 11/2003 | Jenkins et al. ................. 606/41 |
| 6,771,996 | B2 * | 8/2004 | Bowe et al. ................... 600/374 |

FOREIGN PATENT DOCUMENTS

| | | |
|---|---|---|
| EP | 0 928 601 A2 | 7/1999 |
| EP | 0 985 423 A2 | 3/2000 |
| EP | 1120082 A1 | 8/2001 |
| WO | WO00/67832 | 11/2000 |
| WO | WO01-37925 | 5/2001 |

* cited by examiner

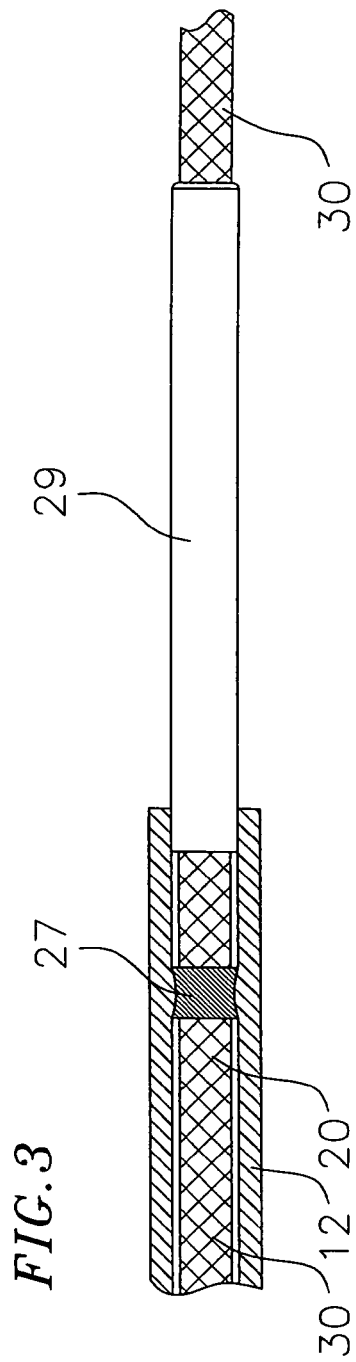
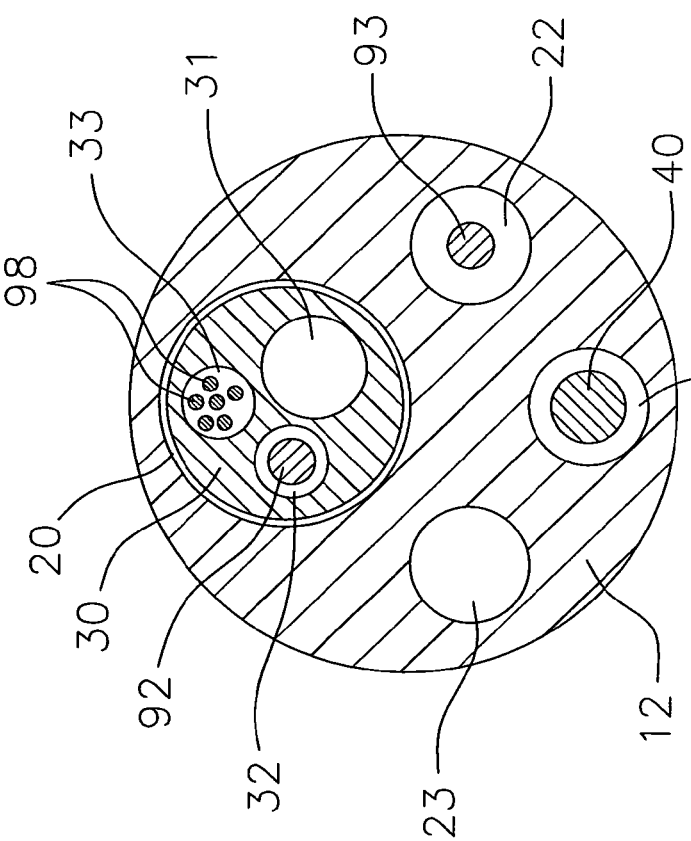

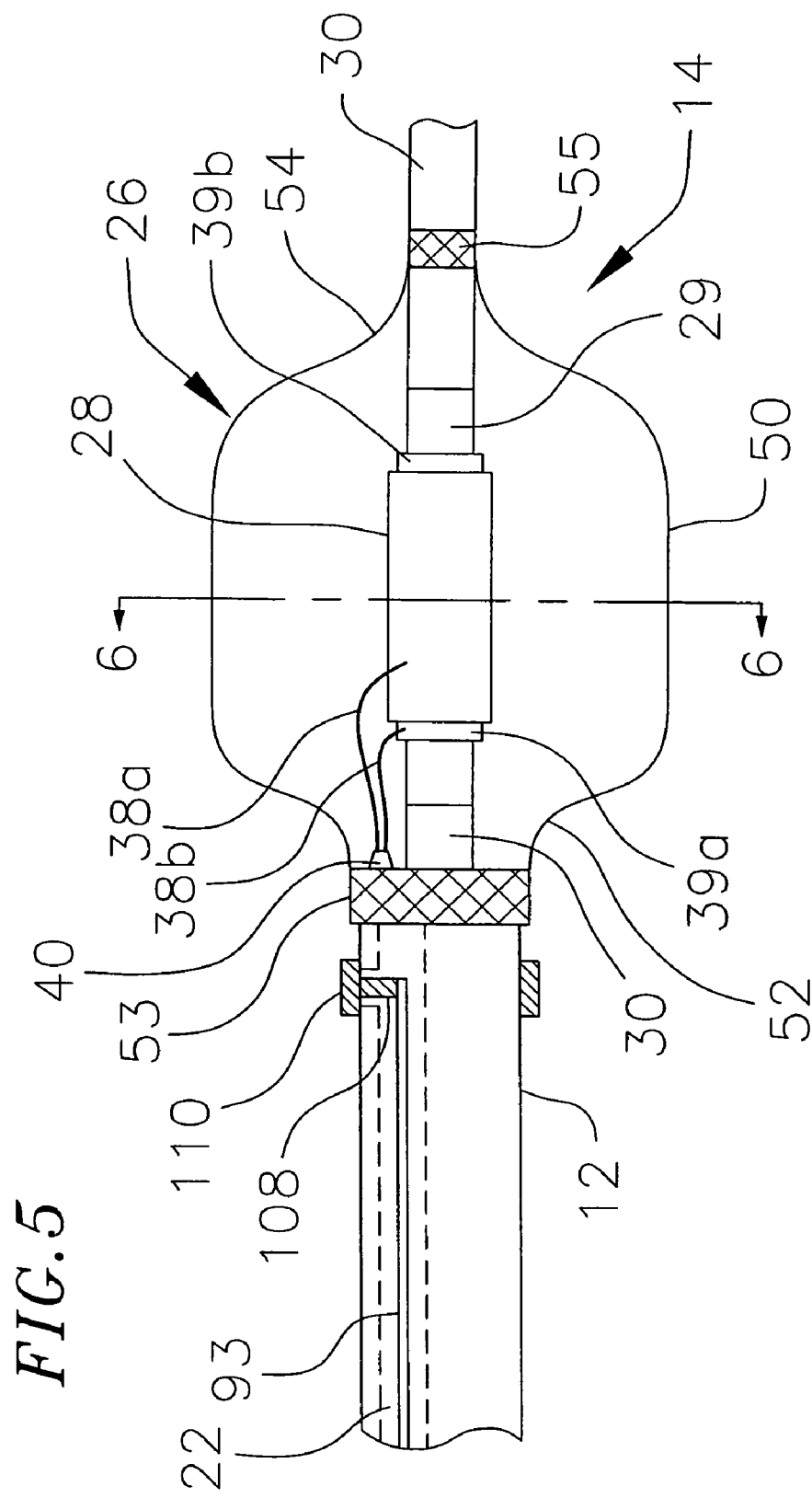

ABLATION CATHETER HAVING STABILIZING ARRAY

CROSS-REFERENCE TO RELATED APPLICATION(S)

This application is a divisional of U.S. patent application Ser. No. 10/201,052, filed on Jul. 23, 2002, now U.S. Pat. No. 6,866,662 issued on Mar. 15, 2005, the contents of which are hereby incorporated by reference.

FIELD OF THE INVENTION

The present invention relates to an improved ablation catheter that is particularly useful for ablating tissue in a tubular region of or near the heart.

BACKGROUND OF THE INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, although such pharmacological solutions are not generally believed to be entirely effective in many cases, and may in some cases result in proarrhythmia and long term inefficacy. Several surgical approaches have also been developed with the intention of treating atrial fibrillation. One particular example is known as the "maze procedure," as is disclosed by Cox, J L et al. in "The surgical treatment of atrial fibrillation. I. Summary" Thoracic and Cardiovascular Surgery 101(3), pp. 402-405 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium.

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While the "maze" procedure as reported by Cox and others has met some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Success with surgical interventions through atrial segmentation, particularly with regard to the surgical "maze" procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and/or left atrial chambers are disclosed in U.S. Pat. Nos. 5,427,119, 5,497,119, 5,564,440, and 5,575,766 to Swartz et al., the disclosures of which are incorporated herein by reference. In addition, various energy delivery modalities have been disclosed for forming such atrial wall lesions, and include use of microwave, laser, and more commonly, radiofrequency energies to create conduction blocks along the cardiac tissue wall, as disclosed in WO 93/20767 to Stem et al., U.S. Pat. No. 5,104,393 to Isner et al., and U.S. Pat. No. 5,575,766 to Swartz et al, respectively, the disclosures of which are incorporated herein by reference.

In addition to attempting atrial wall segmentation with long linear lesions for treating atrial arrhythmia, ablation catheter devices and methods have also been disclosed that are intended to ablate arrhythmogenic tissue of the left-sided accessory pathways, such as those associated with the Wolff-Parkinson-White syndrome, through the wall of an adjacent region along the coronary sinus. For example, Fram et al., in "Feasibility of RF Powered Thermal Balloon Ablation of Atrioventricular Bypass Tracts via the Coronary Sinus: In vivo Canine Studies," PACE, Vol. 18, p 1518-1530 (1995), disclose attempted thermal ablation of left-sided accessory pathways in Jo dogs using a balloon that is heated with bipolar radiofrequency electrodes positioned within the balloon. Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger C D et al., Circulation (1992) 86:947-954; and "Percutaneous laser balloon coagulation of accessory pathways", McMath L P et al., Diagn Ther Cardiovasc Interven 1991; 1425:165-171.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways. One example of a focal ablation method intended to destroy and thereby treat focal arrhythmia originating from a pulmonary vein is disclosed by Haissaguerre, et al. in "Right and Left Atrial Radiofrequency Catheter Therapy of Paroxysmal Atrial Fibrillation" in Journal of Cardiovascular Electrophysiology 7(12), pp. 1132-1144 (1996). In another focal ablation example, Jais et al. in "A focal source of atrial fibrillation treated by discrete radiofrequency ablation" Circulation 95:572-576 (1997) applies an ablative technique to patients with paroxysmal arrhythmias originating from a focal source.

U.S. Pat. Nos. 6,024,740 and 6,117,101 disclose catheters for ablating a circumferential lesion in the pulmonary vein or other region. The catheters include a circumferential ablation element comprising an expandable balloon and an ablation element, such as an ultrasound transducer, coupled to the expandable balloon. The ablation element couples to the balloon's outer skin to ablate a circumferential path of tissue engaged to the balloon. This arrangement has been found effective for creating the desired circumferential ablation. However, it would be desirable to provide a mechanism to enhance stabilization of the ablation element in the pulmonary vein or other region. It would also be desirable to provide a mechanism for mapping and/or recording electrical activity in the region to be ablated, both before and after ablation.

SUMMARY OF THE INVENTION

The present invention is directed to an improved catheter having a circumferential ablation element that includes a mechanism for enhancing the stabilization of the ablation element and optionally for mapping and/or recording electrical activity. The inventive catheter is particularly useful for treatment within a tubular region of or near the heart, e.g., a pulmonary vein, the coronary sinus, the superior vena cava, or the pulmonary outflow tract.

In one embodiment, the invention is directed to a circumferential ablation catheter comprising an elongated tubular catheter body having an outer wall, proximal and distal ends, and at least one lumen extending therethrough. An ablation assembly is mounted at the distal end of the catheter body. The ablation assembly comprises a circumferential ablation element mounted on the distal end of the catheter body and an inflatable balloon provided in surrounding relation to the circumferential ablation element. The inflatable balloon is adjustable between a radially collapsed position and a radially expanded position. The circumferential ablation element preferably comprises an ultrasound ablation element secured to the catheter at a fixed position within the inflatable balloon, wherein the ultrasound ablation element is adapted to emit a substantially circumferential pattern of ultrasound energy and to ablatively couple to a substantial portion of a circumferential region of tissue engaged by the inflatable balloon in the radially expanded position when the ultrasound ablation element is coupled to and actuated by an ultrasound ablation actuator. A stabilization assembly is mounted on the catheter distal to the ablation assembly. The stabilization assembly is designed to be capable of contacting a plurality of points about an inner circumference of a generally tubular region of or near the heart, and thus serves to stabilize the distal end of the catheter during ablation. The stabilization assembly preferably includes one or more electrodes that can be used for mapping and/or recording electrical activity in the inner circumference of the generally tubular region of or near the heart.

In another embodiment, the invention is directed to a method for treating atrial arrhythmia by ablating a substantial portion of a circumferential region of tissue in a tubular region of or near the heart of a patient. The method comprises introducing into a patient a catheter as described above, wherein the circumferential ablation element comprises an ultrasound ablation element coupled to an acoustic energy driver, so that the stabilization assembly is within the tubular region and in contact with a plurality of points about a circumference of the tubular region. A substantial portion of the circumferential region of tissue is contacted with at least a portion of the inflatable balloon, such that the ultrasound ablation element is positioned to deliver a substantially circumferential pattern of ultrasound energy through the inflatable balloon to the substantial portion of the circumferential region of tissue. The acoustic energy driver is activated to ablatively couple the ultrasound ablation element to the substantial portion of the circumferential region of tissue via the inflatable balloon.

DESCRIPTION OF THE DRAWINGS

These and other features and advantages of the present invention will be better understood by reference to the following detailed description when considered in conjunction with the accompanying drawings wherein:

FIG. 2 is an end cross-sectional view of the catheter body of FIG. 1 along line 2-2.

FIG. 3 is a side view of a portion of the catheter according to FIG. 1 showing the junction of the inner support member and the catheter body.

FIG. 5 is a side schematic view of the ablation assembly of the catheter of FIG. 1.

DETAILED DESCRIPTION

Figure 1:
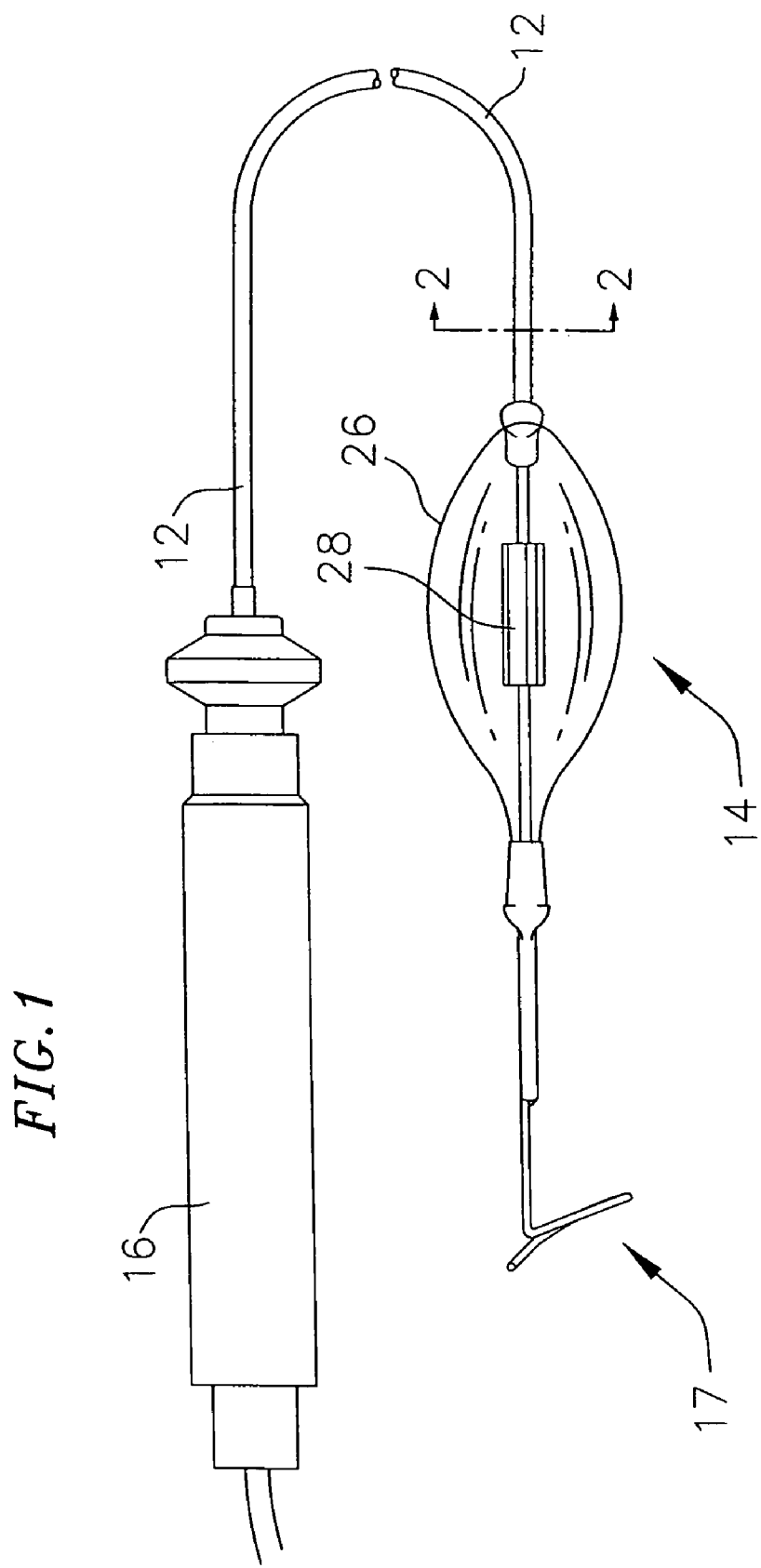
FIG. 1 is a side cross-sectional view of an embodiment of the catheter of the invention.

In an exemplary embodiment of the invention, there is provided a catheter for ablating a circumferential region of tissue, such as a pulmonary vein wall, having a stabilizing array at its distal end. As shown in FIG. 1, the catheter comprises an elongated catheter body 12 having proximal and distal ends, an ablation assembly 14 at the distal end of the catheter body, a control handle 16 at the proximal end of the catheter body, and a stabilization assembly 17 mounted at the distal end of the catheter distal to the ablation assembly. In a preferred embodiment, the stabilization assembly 17 also provides recording, mapping and/or ablating capabilities.

In the depicted embodiment, the catheter body 12 comprises an elongated tubular construction having four lumens extending therethrough. The catheter body 12 is flexible, i.e., bendable, but substantially non-compressible along its length. The catheter body 12 can be of any suitable construction and made of any suitable material. A presently preferred construction comprises polyurethane or PEBAX having an imbedded braided mesh of stainless steel or the like to increase torsional stiffness of the catheter body 12 so that, when the handle 16 is rotated, the distal end of the catheter will rotate in a corresponding manner. The outer diameter of the catheter body 12 is not critical, but preferably ranges from about 5 french to about 10 french, more preferably from about 7 french to about 9 french.

The number and sizes of the lumens in the catheter body 12 can vary as desired depending on the components that extend through the catheter body. In the embodiment depicted in FIG. 2, the first lumen 20, which is the largest lumen, is used as a guidewire lumen and preferably is adapted to slideably receive guidewires (not shown) ranging from about 0.010 inch to about 0.038 inch in diameter. The first lumen 20 also optionally carries a puller wire 92 for deflection of the stabilization assembly 17 and/or electrode lead wires 98 for electrical connection to electrodes on the stabilization assembly, as described further below. The second lumen 21, which is the next largest in size, carries a coaxial cable 40 that is connected to a transducer 28 in the ablation assembly 14. The third lumen 22 carries other lead wires, thermocouple wires, a puller wire and/or any other desired wires (not shown) as desired depending on the particular application for which the catheter is to be used. The fourth lumen 23, which serves as an inflation lumen, is an open lumen to permit fluid to enter and exit the catheter for inflation and deflation of a balloon 26 that is part of the ablation assembly 14. The specific components carried in the lumens are discussed in more detail below. In one preferred embodiment, the first lumen 20 has a diameter of approximately 0.05 inch, the second lumen 21 has a diameter of approximately 0.03 inch, and the third lumen 22 and fourth lumen 23 each have a diameter of approximately 0.028 inch. In an alternative embodiment (not shown), the catheter body 12 can have a single lumen extending through most of its length with a distal region having multiple lumens through which the different components extend. Other modifications to the size and number of lumens, as well as to the arrangement of components in the lumens, are within the scope of the invention.

The useful length of the catheter, i.e., that portion that can be inserted into the body, can vary as desired. Preferably the useful length ranges from about 110 cm to about 130 cm. In one more detailed construction, the proximal end of the catheter body 12 is adapted to be more stiff, preferably at least 30% more stiff, than the distal end of the catheter body. With this design, the proximal end is suitably adapted to provide push transmission to the distal end, while the distal end portion is suitably adapted to track through bending anatomy during in vivo delivery of the distal end portion of the device into the desired ablation region. In a particularly preferred construction, the proximal end of the catheter body comprises a 63D PEBAX tubing having a length ranging from about 100 cm to about 125 cm, and the distal end of the catheter body comprises a 40D PEBAX tubing having a length ranging from about 1 cm to about 12 cm.

The ablation assembly 14, which is mounted at the distal end of the catheter body 12, is shown in detail in FIGS. 3 to 6. The ablation assembly comprises an expandable balloon 26, a circumferential ablation element 28 that is acoustically coupled to the expandable balloon, and an inner support member 30 over which is mounted the ablation member and balloon.

Figure 11:
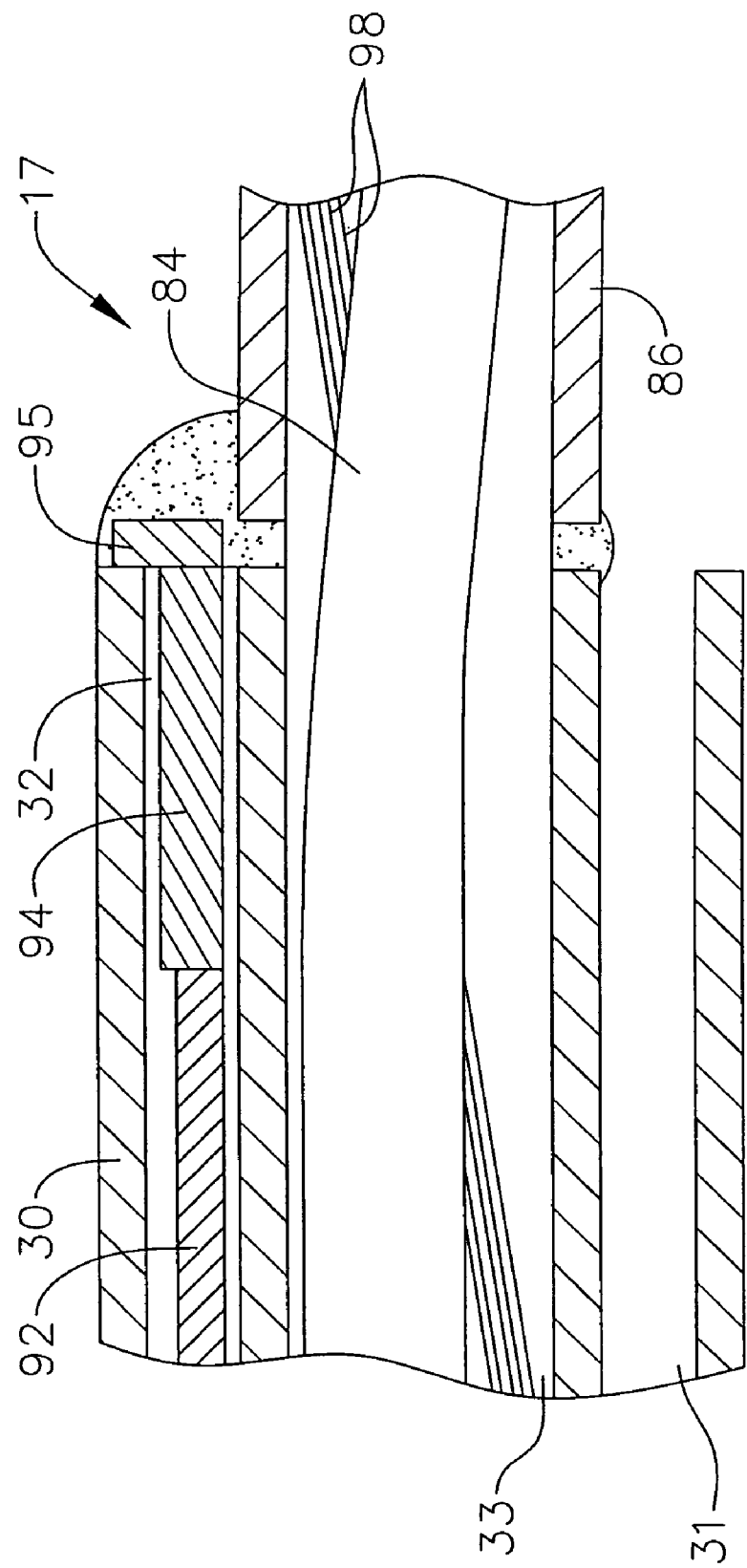
FIG. 11 is a side cross-sectional view of the junction between the inner support member and the stabilization assembly.

The inner support member 30 forms the distal region for the first (guidewire) lumen 20 and also provides support for the circumferential ablation element 28 and for the distal neck of the expansion balloon, as described further below. In a preferred embodiment, the inner support member 30 comprises a braided polyimide (or other plastic) tubing, i.e., polyimide having a braided stainless steel mesh or the like embedded therein. As shown in FIG. 3, the proximal end of the inner support member 30 extends into the distal end of the first lumen 20 of the catheter body 12 any desired length. For example, if the catheter body 12 comprises a more flexible tubing at its distal end, the proximal end of the inner support member preferably extends all of the way through the more flexible tubing and into the distal end of the less flexible tubing, thereby providing a smooth junction inside the corresponding lumens of the tubings. Alternatively, a liner (not shown) or second piece of tubing can be used to achieve the smooth junction. In the depicted embodiment, the inner support member 30 is generally tubular and has three lumens extending therethrough. The first lumen 31 of the inner support member 30 is used to carry a guidewire and is open at its distal end, as shown in FIG. 11. The second and third lumens 32 and 33 of the inner support member 30 carry additional components for the stabilization assembly 17, as discussed further below. As would be recognized by one skilled in the art, the number and arrangement of lumens in the inner support member 30 can vary as desired. For example, a guidewire lumen can extend coaxially through the inner support member with one or more additional lumens arranged coaxially around the first lumen for carrying additional components, as is generally known in the art.

In the depicted embodiment, a metal tubing 29, preferably comprising stainless steel, is mounted around the portion of the inner support member 30 on which the transducer 28 is mounted. The metal tubing 29 preferably has a rigidity similar to that of the transducer 28 and provides a rigid support for the transducer. As also shown in FIG. 3, a marker band 27, preferably made of platinum or the like, is mounted on the portion of the inner support member 30 that extends within the first lumen 21 of the catheter body 12. The marker band 27 is provided for the user to locate the proximal end of the balloon. The location, position and number of marker bands can vary as desired. If desired, a plastic, preferably silicone, tubing (not shown) is provided over the metal tubing 29 to serve as a cushion between the metal tubing and the transducer 28.

Figure 4:
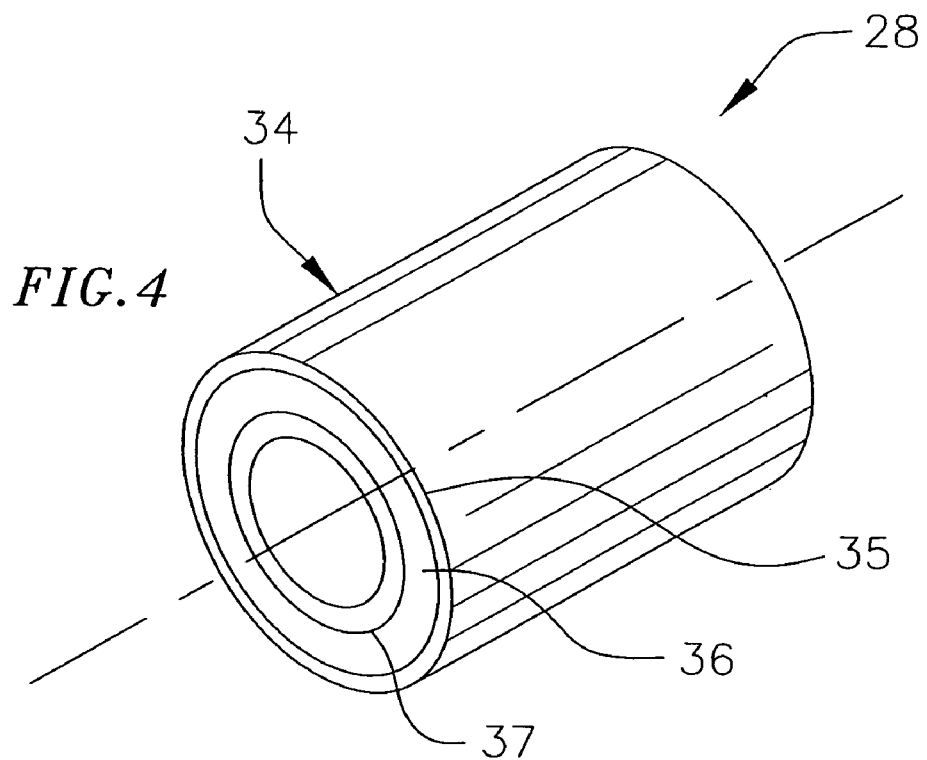
FIG. 4 is a perspective view of a transducer for use in an ablation assembly of a catheter according to the invention.

The ablation member, which is illustrated in FIGS. 4 and 5, takes the form of an annular ultrasonic transducer 28. In the illustrated embodiment, the annular ultrasonic transducer has a unitary cylindrical shape with a hollow interior (i.e., is tubular shaped). However, the transducer 28 can have a generally annular shape and be formed of a plurality of segments. For instance, the transducer can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments which are arranged in a polygon-shape (e.g., hexagon). In addition, although in the illustrated embodiment the ultrasonic transducer comprises a single transducer element, the transducer can be formed of a multi-element array.

As is shown in detail in FIG. 4, the ultrasound transducer 28 includes a tubular wall 34 that includes three concentric tubular layers. The central layer 36 is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. (East Hartford, Conn.) and from Valpey-Fischer Corp. (Hopkinton, Mass.). The outer and inner tubular layers 35 and 37 enclose the central layer 36 within their coaxial space and are each constructed of an electrically conductive material, thereby forming transducer electrodes. In the illustrated embodiment, these transducer layers or electrodes 35 and 37 each comprise a metallic coating, and more preferably a coating of nickel, copper, silver, gold, platinum, or an alloy thereof.

The length of the transducer 28 (or multi-element array of transducer elements that forms the transducer) desirably is selected for a given clinical application. In connection with forming circumferential condition blocks in cardiac or pulmonary vein wall tissue, the transducer length preferably ranges from about 2 mm to about 10 mm, more preferably from about 5 mm to about 10 mm. A transducer accordingly sized is believed to form a lesion of a width sufficient to ensure the integrity of the formed conductive block without undue tissue ablation. For other applications, however, the length can be significantly longer.

Likewise, the outer diameter of the transducer 28 desirably is selected to account for delivery through a particular access path (e.g., percutaneously or transeptally), for proper placement and location within a particular body space, and for achieving a desired ablation effect. In a preferred application within or near the pulmonary vein ostium, the transducer 28 preferably has an outer diameter ranging from about 1.8 mm to about 2.5 mm or greater. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer 28 may have an outer diameter ranging from about 1 mm to about 2 cm, depending on the application.

The central layer 36 of the transducer 28 has a thickness selected to produce a desired operating frequency. The operating frequency will vary depending upon clinical needs, such as the tolerable outer diameter of the ablation and the depth of heating, as well as upon the size of the transducer as limited by the delivery path and the size of the target site. As described in greater detail below, the transducer 28 in the illustrated embodiment preferably operates at a frequency ranging from about 5 MHz to about 20 MHz, and more preferably from about 7 MHz to about 10 MHz. Thus, for example, the transducer can have a thickness of approximately 0.3 mm for an operating frequency of about 7 MHz (i.e., a thickness generally equal to half the wavelength associated with the desired operating frequency).

The transducer 28 is vibrated across the wall thickness and to radiate collimated acoustic energy in the radial direction. For this purpose, as best seen in FIG. 5, electrical transducer leads 38a and 38b are electrically coupled to outer and inner tubular layers 35 and 37, respectively, of the transducer. The electrical transducer lead 38a coupled to the outer tubular layer 35 is preferably soldered directed to the outer tubular member. The electrical transducer lead 38b coupled to the inner tubular layer 37 is preferably indirectly coupled by soldering the lead to a first and second platinum rings 39a and 39b or the like, which is soldered to the proximal end of the inner tubular layer and extends proximally beyond the transducer. The platinum rings 39 serve to "air-back" the transducer 28 to produce more energy and to enhance energy distribution uniformity, as is known in the art. In a preferred embodiment, the electrical leads are 4 to 8 mil (0.004 to 0.008 inch diameter) silver wire or the like.

The proximal ends of the electrical transducer leads 38 are adapted to couple to an ultrasonic driver or actuator (not shown). In a preferred embodiment, a coaxial cable 40 is provided in the second lumen 21 of the catheter body. The proximal ends of the electrical transducer leads 38 are electrically connected to wires in the coaxial cable 40, which is well insulated as to inductance interference. In an alternative embodiment (not shown), the electrical transducer leads 38 can extend through the second lumen 21 of the catheter body, in which case the leads must be well insulated when in close contact. Other configurations for the leads 38 are contemplated within the scope of the invention. For example, the leads 38 may extend through different lumens of the catheter body 12.

The ultrasonic actuator generates alternating current to power the transducer. The ultrasonic actuator drives the transducer at frequencies ranging from about 5 to about 20 MHz, and preferably for the illustrated application ranging from about 7 MHz to about 10 MHz. In addition, the ultrasonic driver can modulate the driving frequencies and/or vary power to smooth or unify the produced collimated ultrasonic beam. For instance, the function generator of the ultrasonic actuator (840) can drive the transducer at frequencies ranging from about 6.8 MHz to about 7.2 MHz by continuously or discretely sweeping between these frequencies.

Figure 6:
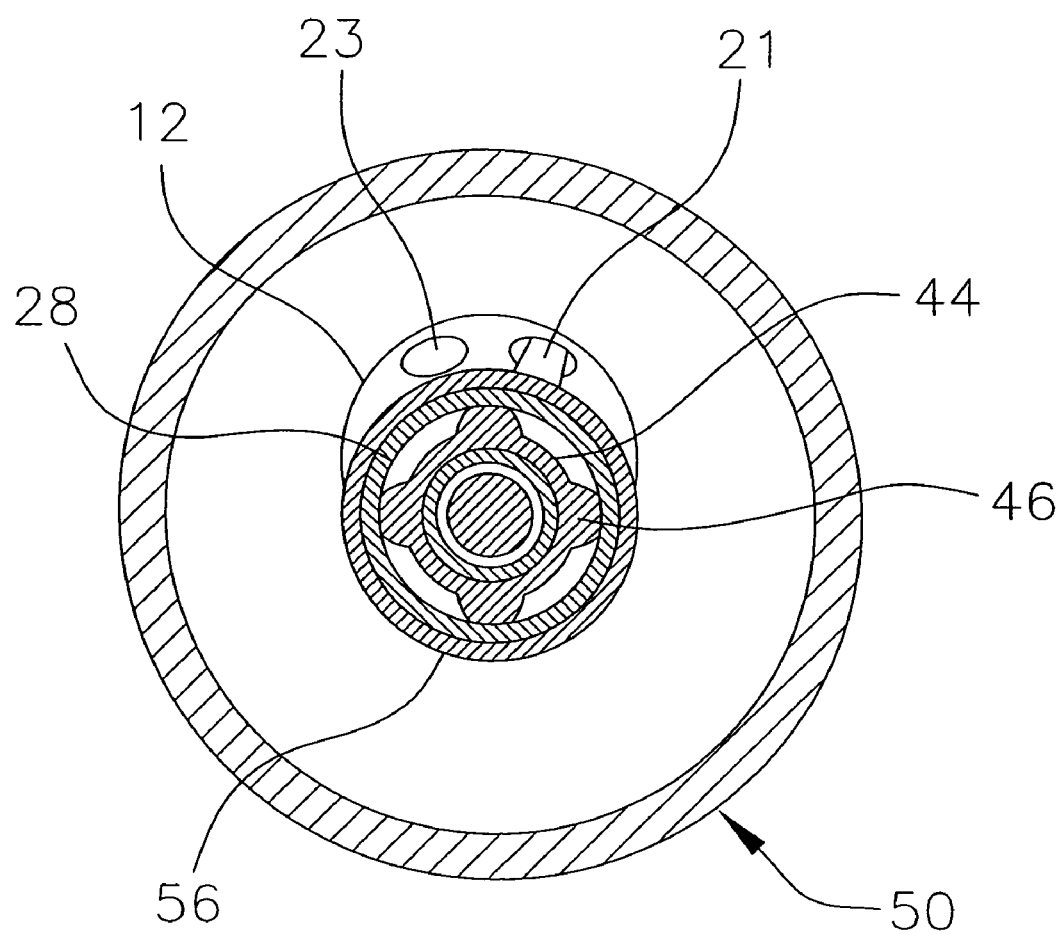
FIG. 6 is an end cross-sectional view of the ablation assembly of FIG. 5 along line 6-6.

In an alternate embodiment, the transducer can be sectored by scoring or notching the outer tubular layer 35 and part of the central layer 36 along lines parallel to the longitudinal axis of the transducer, as illustrated in FIG. 6. In this embodiment, a separate electrical transducer lead 38 connects directly to each sector in order to couple the sector to a dedicated power control that individually excites the corresponding transducer sector. By controlling the driving power and operating frequency to each individual sector, the ultrasonic driver can enhance the uniformity of the ultrasonic beam around the transducer and can vary the degree of heating (i.e., lesion control) in the angular dimension.

In this embodiment, the transducer 28 is "air-backed" because the inner support member 30, including the metal tubing 29 optionally mounted thereon, does not contact an appreciable amount of the inner surface of the inner tubular layer 37. The piezoelectric crystal that forms central layer 36 of the ultrasound transducer is adapted to radially contract and expand (or radially "vibrate") when an alternating current is applied from a current source and across the outer and inner tubular layers 35 and 37 via the electrical transducer leads 38. This controlled vibration emits the ultrasonic energy that is adapted to ablate tissue and form a circumferential conduction block according to the present embodiment. Therefore, it is believed that appreciable levels of contact along the surface of the crystal may provide a dampening effect that would diminish the vibration of the crystal and thus limit the efficiency of ultrasound transmission. Accordingly, in a preferred embodiment, the transducer 28 is mounted coaxially about the inner support member 30 in a manner providing a gap between the inner support member and the transducer inner tubular layer 37. Any of a variety of structures can be used to support the transducer 28 about the inner support member 30. For instance, spaces or splines (not shown) can be used to coaxially position the transducer 28 about the inner support member 30 while leaving a generally annular space between the components. In the alternative, one or more O-rings (not shown) can circumscribe the inner support member 30 and lie between the inner support member and the transducer 28 to support the transducer in a manner similar to that illustrated in U.S. Pat. No. 5,606,974, the disclosure of which is incorporated herein by reference. Detailed examples of alternative transducer support structures are disclosed in U.S. Pat. Nos. 6,117,101 and 5,620,479, the disclosures of which are incorporated herein by reference.

Figure 7:
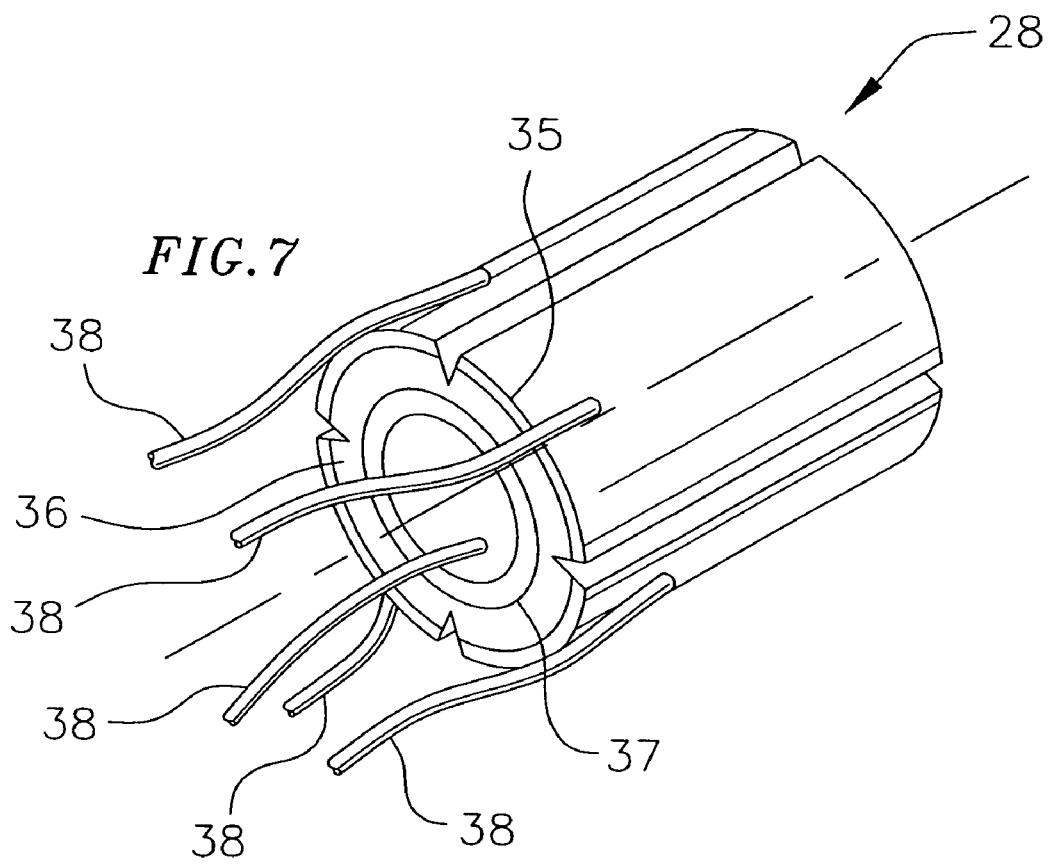
FIG. 7 is a perspective view of an alternative embodiment of a transducer according to the invention.

In the illustrated embodiment, as shown in FIG. 7, a stand-off 44 is provided in order to ensure that the transducer 28 has a radial separation from the inner support member 30 to form a gap filled with air and/or other fluid. The stand-off 44 is a tubular member with a plurality of circumferentially spaced outer splines 46 that hold the majority of the transducer inner surface away from the surface of the stand-off between the splines, thereby minimizing dampening affects from the coupling of the transducer to the catheter. The tubular member that forms the stand-off 44 may also provide its inner bore as a guidewire lumen in the region of the ultrasound transducer. In a further mode, the catheter body 12 can include additional lumens (not shown) that lie either next to or coaxial with the first (guidewire) lumen 20 and that terminate at ports located within the space between the inner member 30 and the transducer 28. A cooling medium can circulate through the space defined by the stand-off 44 between the inner support member 30 and the transducer 28 via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The arrangement of the expandable balloon 26 is shown in FIGS. 5 and 6. The balloon has a primary region 50, which is generally coaxially disposed over the inner support member 30, and proximal and distal neck regions 52 and 54. A proximal adaption 53 seals the proximal neck region 52 over the distal end of the catheter body 12, and a distal adaption 55 seals the distal neck region 54 over the inner support member 30. According to this arrangement, a fluid tight interior chamber is formed within the expandable balloon 26. This interior chamber is fluidly coupled to a pressurizeable fluid source (not shown) via the fourth (inflation) lumen 23. The second (coaxial cable) lumen 21 also communicates with the interior chamber of the expandable balloon 26 so that the ultrasound transducer 28, which is positioned within that chamber and over the inner support member 30, can be electrically coupled to an ultrasound actuator via the coaxial cable extending through the second lumen, as discussed above.

The expandable balloon 26 may be constructed from a variety of known materials, although the balloon preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, silicone, latex, and low durometer polyurethane (for example, a durometer of about 80 A). In addition or in the alternative to constructing the balloon of highly compliant material, the balloon can be formed to have a predefined fully inflated shape (i.e., be pre-shaped) to generally match the anatomic shape of the body lumen in which the balloon is to be inflated. For instance, as described below in greater detail, the balloon can have a distally tapering shape to generally match the shape of a pulmonary vein ostium and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

In a particularly preferred embodiment, the balloon is constructed to exhibit at least 300% expansion at 3 atmospheres of pressure, and more preferably to exhibit at least 400% expansion at that pressure. The term "expansion" refers to the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to the change in diameter that is attributable to the material compliance in a stress strain relationship. In one embodiment, the balloon is adapted to expand under a normal range of pressure such that its outer diameter may be adjusted from a radially collapsed position of about 5 millimeters to a radially expanded position of about 2.5 centimeters (having approximately a 500% expansion ratio).

The transducer 28 may be electrically and mechanically isolated from the interior of the balloon 26. Any of a variety of coatings, sheaths, sealants, tubings and the like may be suitable for this purpose, such as those described in U.S. Pat. Nos. 5,620,479 and 5,606,974. In the illustrated embodiment, a conventional, flexible, acoustically compatible and medical grade epoxy is applied over the transducer 28. The epoxy may be, for example, Epotek 301, Epotek 310, which is available commercially from Epoxy Technology, or Tracon FDA-8. In addition, a conventional sealant (not shown), such as General Electric Silicon II gasket glue and sealant, preferably is applied at the proximal and distal ends of the transducer 28 around the exposed portions of the inner support member 30, electrode transducer leads 38, and stand-off 44 to seal the space between the transducer and the inner support member at these locations.

In a preferred embodiment, as shown in FIG. 7, an ultra thin-walled polyester heat shrink tubing 56 or the like seals the epoxy coated transducer 28. Alternatively, the epoxy covered transducer 28, inner member 30 and stand-off 44 can be inserted into a tight thin wall rubber or plastic tubing (not shown) made from a material such as Teflon®, polyethylene, polyurethane, silastic or the like. The tubing desirably has a thickness ranging from about 0.0005 to about 0.003 inches. Preferably when assembling the ablation device assembly, additional epoxy is injected into the heat shrink tubing 56 after the tubing is placed over the epoxy coated transducer 28. As the heat shrink tubing 56 shrinks, excess epoxy flows out and a thin layer of epoxy remains between the transducer 28 and the tubing. The layers of epoxy and heat shrink tubing 56 protect the surface of the transducer 30, help acoustically match the transducer to the load, make the ablation device more robust, and enhances the airtight integrity of the air backing. Although not illustrated in FIG. 5 in order to simplify the drawing, the heat shrink tubing 56 extends beyond the ends of the transducer 28 and surrounds a portion of the inner support member 30 on either side of the transducer. A filler (not shown) can also be used to support the ends of the heat shrink tubing 56. Suitable fillers include flexible materials such as epoxy, Teflon® tape and the like.

The ultrasound transducer 28 of the present embodiment sonically couples with the outer skin of the balloon 26 in a manner that forms a circumferential conduction block in a pulmonary vein as follows. Initially, the ultrasound transducer 28 is believed to emit its energy in a circumferential pattern that is highly collimated along the transducer's length relative to its longitudinal axis. The circumferential band therefore maintains its width and circumferential pattern over an appreciable range of diameters away from the source at the transducer. Also, the balloon 26 is preferably inflated with fluid (not shown) that is relatively ultrasonically transparent, such as, for example, non-ionic saline or degassed water. In a preferred embodiment, the inflation fluid comprises a radiopaque dye, such as Omnipaque 360 (commercially available from Nycomed), and more preferably a 70:30 mixture of saline and non-ionic contrast solution, so that the position of the transducer can be determined using fluoroscopy. By actuating the transducer 28 while the balloon 26 is inflated, the circumferential band of energy is allowed to translate through the inflation fluid and ultimately sonically couple with a circumferential band of balloon skin that circumscribes the balloon. Moreover, the circumferential band of balloon skin material may also be further engaged along a circumferential path of tissue that circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated. The energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

In one particular balloon-transducer combination, the ultrasound transducer preferably has a length such that the ultrasonically coupled band of the balloon skin, having a similar length according to the collimated electrical signal, is shorter than the working length of the balloon. According to this aspect of the relationship, the transducer is adapted as a circumferential ablation element that is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably is less than one-half the working length of the balloon. By sizing the ultrasonic transducer length smaller than the working length of the balloon—and hence shorter than a longitudinal length of the engagement area between the balloon and the wall of the body space (e.g., pulmonary vein ostium)—and by generally centering the transducer within the balloon's working length, the transducer operates in a field isolated from the blood pool. A generally equatorial position of the transducer relative to the ends of the balloon's working length also assists in the isolation of the transducer from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the catheter body 12 may include an additional radiopaque marker or markers (not shown) to identify the location of the transducer 28 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The use and placement of a suitable radiopaque marker for use in the present invention is described in U.S. Pat. No. 6,117,101, the disclosure of which is incorporated herein by reference.

If desired, one or more temperature sensing devices (not shown) are provided for monitoring the temperature on and around the ablation assembly 14. For example, temperature sensing devices, such as thermocouples, can be used for measuring the temperature of the inflation fluid inside the balloon 26, for measuring the temperature of the transducer 28, and/or for measuring the temperature of the tissue during ablation.

The balloon 26 of the ablation assembly 14 functions to stabilize the ablation assembly within the region to be ablated, and particularly in a tubular region of or near the heart, such as the pulmonary vein. To enhance the stabilization of the ablation assembly 14, a stabilization assembly 17 is mounted at the distal end of catheter, distal to the ablation assembly 14, as shown in FIGS. 1 and 11 to 15. The stabilization assembly 17 is preferably a structure that, in use, can have multiple locations in contact with the inner circumference of a tubular region of or near the heart, and more preferably that includes a generally-circular structure that has an outer circumference that can contact a majority of the inner circumference of such a tubular region.

In the depicted embodiment, the stabilization assembly 17 comprises a support member 84 covered by a non-conductive covering 86. The stabilization assembly 17 comprises a generally straight proximal region 88, a generally circular main region 89 and a generally straight distal region 90. The proximal region 88 is mounted on the distal end of the inner support member 30, as described in more detail below. The proximal region 88 preferably has an exposed length, e.g., not contained within the inner support member 30, ranging from about 3 mm to about 12 mm, more preferably about 3 mm to about 8 mm, still more preferably about 5 mm inch, but can vary as desired.

Figure 12:
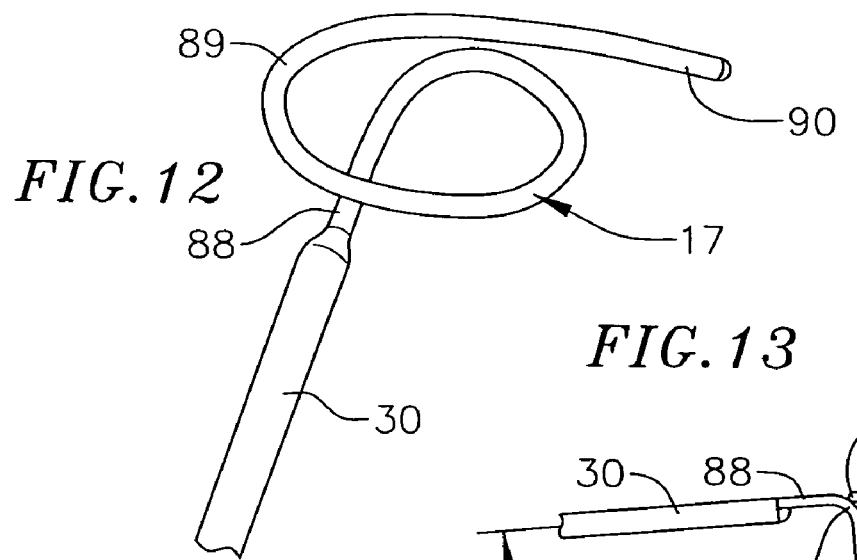
FIG. 12 is a schematic perspective view of the mapping assembly according to the invention.
Figure 13:
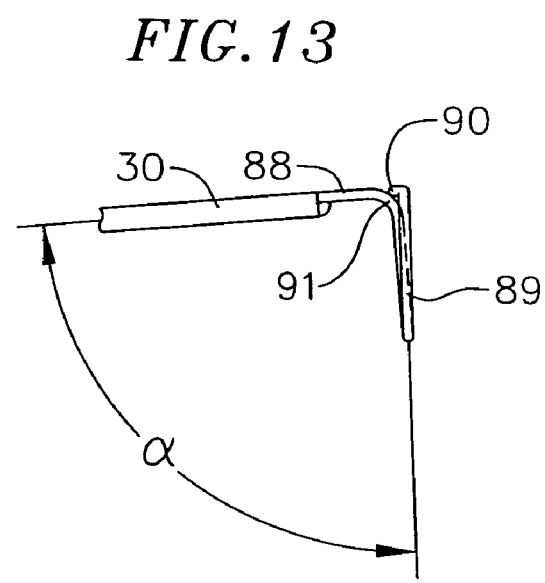
FIG. 13 is a side view of the stabilization assembly according to the invention in a clockwise formation.
Figure 14:
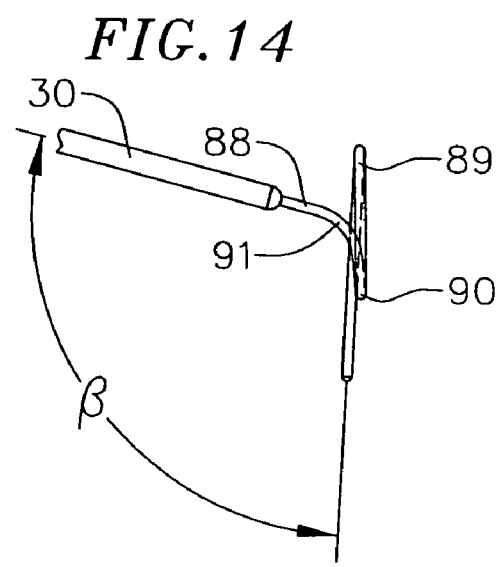
FIG. 14 is a side view of the stabilization assembly according to the invention in a counterclockwise formation rotated 90° relative to the assembly depicted in FIG. 5.

The generally circular main region 89 does not form a flat circle, but is very slightly helical, as shown in FIGS. 12 to 14. The main region 89 has an outer diameter preferably ranging from about 10 mm to about 35 mm, more preferably from about 12 mm to about 25 mm, still more preferably from about 15 mm to about 20 mm. The transition region 91 of the straight proximal region 88 and generally circular main region 89 is slightly curved and formed such that, when viewed from the side with the proximal region at the top of the circular main region as shown in FIG. 5, the proximal region (along with the inner support member 30) forms an angle α with the curved region ranging from about 75° to about 95°, preferably from about 83° to about 93°, more preferably about 87°. The main region 89 can curve in a clockwise direction, as shown in FIG. 13, or a counterclockwise direction, as shown in FIG. 14. When the stabilization assembly 17 is turned 90°, as shown in FIG. 14, so that the transition region 91 is near the center of the main region, the proximal region (along with the inner support member 30) forms an angle β with the main region ranging from about 90° to about 135°, preferably from about 100° to about 110°, more preferably about 105°.

The support member 84 is made of a material having shape-memory, i.e., that can be straightened or bent out of its original shape upon exertion of a force and is capable of substantially returning to its original shape upon removal of the force. A particularly preferred material for the support member 84 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability. The non-conductive covering 86 can be made of any suitable material, and is preferably made of a biocompatible plastic such as polyurethane or PEBAX. If desired, the support member 84 can be eliminated and the distal end of the non-conductive covering 86 can be pre-formed to have the desired curve of the stabilization assembly 17.

In a particularly preferred embodiment, the stabilization assembly 17 can also function as a mapping, recording and/or ablating assembly. In this embodiment, a series of ring electrodes 96 are mounted on the non-conductive covering 86 of the generally circular main region 89 of the stabilization assembly 17. The ring electrodes 96 can be made of any suitable solid conductive material, such as platinum or gold, preferably a combination of platinum and iridium, and mounted onto the non-conductive covering 86 with glue or the like. Alternatively, the ring electrodes 96 can be formed by coating the non-conductive covering 86 with an electrically conducting material, like platinum, gold and/or iridium. The coating can be applied using sputtering, ion beam deposition or an equivalent technique.

In a preferred embodiment, each ring electrode 96 is mounted by first forming a hole in the non-conductive covering 86. An electrode lead wire 98 is fed through the hole, and the ring electrode 96 is welded in place over the lead wire and non-conductive covering 86. The lead wires 98 extend between the non-conductive covering 86 and the support member 84. The proximal end of each lead wire 98 is electrically connected to a suitable connector (not shown), which is connected to a suitable monitor, recording device and/or source of ablation energy (not shown).

Figure 15:
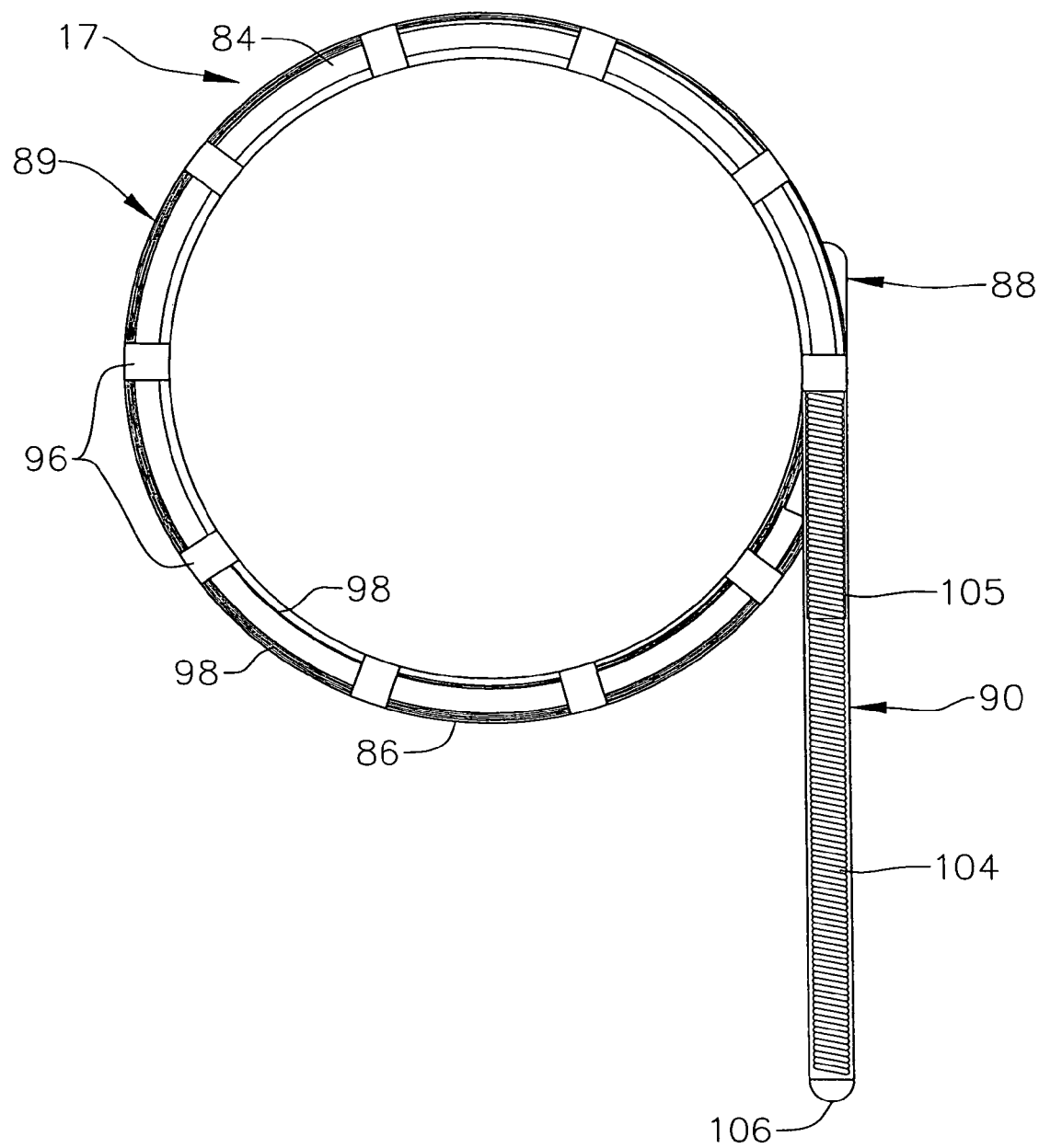
FIG. 15 is a schematic view of the stabilization assembly according to the invention.

The number of ring electrodes 96 on the stabilization assembly 17 can vary as desired. Preferably the number of ring electrodes 96 ranges from about four to about twenty, more preferably from about eight to about twelve. In a particularly preferred embodiment, the stabilization assembly 17 carries ten ring electrodes 96. The ring electrodes 96 are preferably approximately evenly spaced around the generally circular main region 89, as best shown in FIG. 15. In a particularly preferred embodiment, a distance of approximately 5 mm is provided between the centers of the ring electrodes 96.

Figure 16:
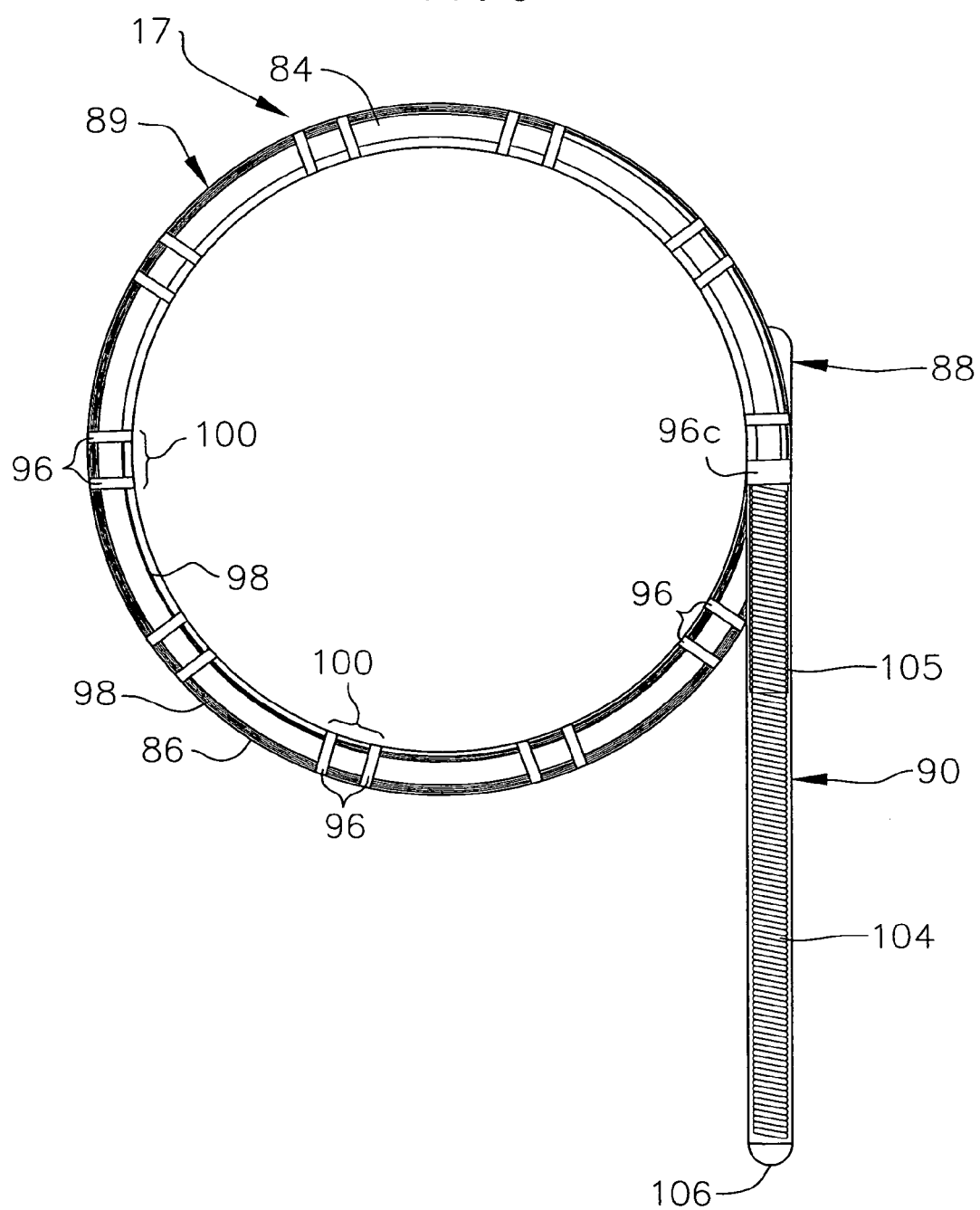
FIG. 16 is a schematic view of an alternative stabilization assembly according to the invention.

An alternative electrode arrangement is depicted in FIG. 16. In this embodiment, which is particularly useful for mapping and/or recording, the stabilization assembly includes a series of ring electrode pairs 100. Each ring electrode pair 100 comprises two closely-spaced ring electrodes 96. As used herein, the term "ring electrode pair" refers to a pair of ring electrodes that are arranged closer to each other than they are to the other adjacent ring electrodes. Preferably the distance between two electrodes 96 of an electrode pair 100 is less than about 3 mm, more preferably less than about 2 mm, still more preferably from about 0.5 mm to about 1.5 mm. The number of electrode pairs 100 can vary as desired, and preferably ranges from 2 to 14 pairs, more preferably 10 pairs. In a particularly preferred embodiment, the stabilization assembly 17 carries 10 pairs of electrodes with a space of approximately 1 mm between the two electrodes 96 of each pair 100.

Preferably each ring electrode 96 is relatively short, having a length ranging from about 0.4 mm to about 0.75 mm, with the most distal ring electrode 96c being longer than the other ring electrodes, preferably having a length ranging from about 1 mm to about 1.5 mm. The longer ring electrode provides a signal to the user when the catheter is being viewed under fluoroscopy. Specifically, because the mapping assembly is generally circular, it can be difficult for the user to determine which electrodes are placed at a particular location in the heart. By having one ring electrode, such as the most distal ring electrode, sized differently from the other ring electrodes, the user has a reference point when viewing the catheter under fluoroscopy.

Regardless of the size and number of the ring electrodes 96, the electrode pairs 100 are preferably approximately evenly spaced around the generally circular main region 89. The closely-spaced electrode pairs 100 allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the stabilization assembly 17 is placed in the pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium by the electrical signal. If desired, additional electrodes (not shown) could be mounted along the inner support member 30, the generally straight proximal section 89, the transition region 91, and generally straight distal region 90.

Other electrode arrangements suitable for mapping, recording and/or ablation can be provided on the stabilization assembly in accordance with the invention. Examples of arrangements suitable for ablation procedures are described in U.S. patent application Ser. No. 10/118,680, entitled "Catheter Having Circular Ablation Assembly," the disclosure of which is incorporated herein by reference.

The generally straight distal region 90 is preferably provided with an atraumatic design to prevent the distal end of the stabilization assembly 17 from penetrating tissue, particularly when the catheter is being introduced into the patient. In the depicted embodiment, the distal region 90 comprises a tightly wound coil spring 104 made, for example, of stainless steel, such as the mini guidewire commercially available from Cordis Corporation (Miami, Fla.) or a coil having a 0.0045 inch wire size and a 0.009 inch inner diameter, such as that commercially available from Microspring. The coil spring 104 is mounted at its proximal end in a short piece of tubing 105 with polyurethane glue or the like, which is then glued or otherwise anchored within the non-conductive covering 86. The tubing 105 is less flexible than the non-conductive covering 86 but more flexible than that support member 84 to provide a transition in flexibility along the length of the stabilization assembly 17. The distal end of the distal region 90 is capped, preferably with polyurethane glue 106, to prevent body fluids from entering the stabilization assembly 17. In the depicted embodiment, the generally straight distal region 90 has a length of about 0.5 inch, but can be any desired length, for example, ranging from about 0.25 inch to about 1.0 inch. Any other atraumatic tip design that prevents the distal end of the mapping assembly from penetrating tissue could be provided. An alternative design in the form of a soft plastic ball is described in U.S. Pat. No. 6,371,955, the entire disclosure of which is incorporated herein by reference. Additionally, if desired, the distal region 90 can be formed, at least in part, of a radiopaque material to aid in the positioning of the stabilization assembly 17 under fluoroscopy.

Other constructions for the stabilization assembly 17 can be provided in accordance with the invention. For example, the stabilization assembly can comprise an expandable basket-shaped arrangement having a plurality of spines, preferably including one or more electrodes on each spine. Such structures are describes in U.S. Pat. Nos. 5,411,025, 5,772,590, 5,628,313, 6,292,695, and U.S. patent application Ser. No. 10/017,029, filed Dec. 14, 2001, entitled "Basket Catheter with Multiple Location Sensors," the disclosures of which are incorporated herein by reference.

The junction of the inner support member 30 and stabilization assembly 17 is shown in FIG. 11. The non-conductive covering 86 is attached to the braided polyimide tubing of the inner support member 30 by glue or the like. The Nitinol support member 84 extends from the third lumen 33 of the polyimide tubing into the non-conductive covering 86. The proximal end of the support member 84 terminates a short distance within the third lumen 33, approximately about 5 mm. However, if desired, the proximal end of the support member 84 can extend further into the third lumen 33 or into the catheter body 12. The lead wires 98 attached to the ring electrodes 96 also extend through the third lumen 33 of the inner support member 30 and through a lumen of the catheter body 12, and terminate at their proximal end in a connector (not shown).

A puller wire 92 is provided for deflection of the catheter proximal to the stabilization assembly 17. The puller wire 92 extends through the second lumen 32 of the inner support member 30, which is an off-axis lumen, and through the first lumen 20 of the catheter body 12. Preferably the puller wire 92 is anchored at its distal end to the distal end of the inner support member 30 near the junction with the stabilization assembly 17, as shown in FIG. 11. Specifically, a T-shaped anchor is formed, which comprises a short piece of tubular stainless steel 94, e.g., hypodermic stock, which is fitted over the distal end of the puller wire 92 and crimped to fixedly secure it to the puller wire. The distal end of the tubular stainless steel 94 is fixedly attached, e.g., by welding, to a cross-piece 95 formed of stainless steel ribbon or the like. The cross-piece 95 sits beyond the distal end of the second lumen 32. The cross-piece 95 is larger than the lumen opening and, therefore, cannot be pulled through the opening. The distal end of the second lumen 32 is then filled with glue or the like, preferably a polyurethane glue. Within the second lumen 32 of the inner support member 30, the puller wire 92 may extend through a plastic, preferably Teflon®, puller wire sheath (not shown), which prevents the puller wire from cutting into the wall of inner support member when the inner support member is deflected.

The puller wire 92 is made of any suitable metal, such as stainless steel or Nitinol, and is preferably coated with Teflon® or the like. The coating imparts lubricity to the puller wire 92. The puller wire 92 preferably has a diameter ranging from about 0.006 to about 0.010 inch. In a preferred embodiment, a compression coil (not shown) is situated within the catheter body 12 in surrounding relation to the puller wire 92. The compression coil is made of any suitable metal, preferably stainless steel, and is tightly wound on itself to provide flexibility, i.e., bending, but to resist compression. An example of a catheter construction including a puller wire and compression coil suitable for use in the present invention is disclosed in U.S. Pat. No. 6,371,955, the disclosure of which is incorporated herein by reference. If desired, the compression coil and puller wire can be enclosed with a protective sheath (not shown) within the catheter body 12 to avoid interfering with a guidewire that extends through the first lumen 20 of the catheter body with the compression coil and puller wire.

Longitudinal movement of the puller wire 92 relative to the catheter body 12, which results in deflection of the stabilization assembly 17, is accomplished by suitable manipulation of the control handle 16. Examples of suitable control handles for use in the present invention are disclosed, for example, in U.S. Pat. No. Re 34,502 and U.S. Pat. No. 5,897,529, the entire disclosures of which are incorporated herein by reference. If desired, a second puller wire (not shown) can be included, for example, for bidirectional deflection of the stabilization assembly 17 or for deflection of the ablation assembly 14. Suitable control handles for use in connection with multiple puller wires are disclosed in U.S. Pat. Nos. 6,123,699, 6,171,277, 6,183,435, 6,183,463, 6,198,974, 6,210,407, and 6,267,746, the disclosures of which are incorporated herein by reference.

If deflection of the ablation assembly 14 is desired, a puller wire 93 can be provided that extends through an off-axis lumen in the catheter body 12, such as the third lumen 22. The distal end of the puller wire 93 is anchored at or near the proximal end of the ablation assembly 14, preferably just proximal to the proximal end of the balloon 26. A preferred method of anchoring the puller wire 93 in this position is shown in FIG. 17. Specifically, a stainless steel hypotube 108 or the like is mounted on the distal end of the puller wire 93. The hypotube 108 extends through an opening in the side wall of the third lumen 22. The hypotube is anchored, by solder or the like, to a ring 110, for example, made of stainless steel or platinum, that is mounted on the outside of the catheter body 12. Suitable control handles for manipulation of the proximal end of the puller wire 93 to cause deflection of the ablation assembly 14 are discussed above.

If desired, a puller wire (not shown) can be provided for altering the diameter of the generally circular main region 89 of the stabilization assembly 17. Such a design is described in U.S. Pat. No. 5,626,136, the disclosure of which is incorporated herein by reference. The control handles described above can also be used for manipulation of a puller wire for contraction of the generally circular main region 89 of the stabilization assembly 17.

In a preferred method in accordance with the invention, the circumferential ablation assembly is positioned at an ablation region, preferably along a tubular region of or near the heart, more preferably along the pulmonary vein, and thereafter a continuous circumferential region of tissue at the ablation region is ablated. The circumferential ablation assembly is preferably introduced into a pulmonary vein of the left atrium according to a transeptal access method. This method generally involves accessing the right venous system using the "Seldinger" technique, whereby a peripheral vein (such as the femoral vein) is punctured with a needle. The puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

Other left atrial access methods may be suitable substitutes for using the circumferential ablation device assembly of the present invention. In one alternative, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to transeptal introduction of the guiding catheter into the left atrium, a guidewire is advanced into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) that is coaxial within the guiding catheter, such as, for example, by using one of the directional catheters disclosed in U.S. Pat. No. 5,575,766, the disclosure of which is incorporated herein by reference. Alternatively, the guidewire may have sufficient stiffness and maneuverability in the left atrial cavity to unitarily subselect the desired pulmonary vein distally of the guiding catheter seated at the fossa ovalis.

Suitable guidewire designs for use in the catheter of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" are particularly suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

The distal end of the catheter is introduced over the guidewire and into the pulmonary vein. The circumferential ablation assembly is positioned at an ablation region of the pulmonary vein where the circumferential conduction block is to be desirably formed. The stabilization assembly is positioned distal to the ablation assembly within the pulmonary vein so that the outer circumference of the assembly is substantially in contact with the inner circumference of the pulmonary vein, thereby stabilizing the distal end of the catheter within the pulmonary vein. Preferably at least about 50%, more preferably at least about 80%, still more preferably at least about 95%, even more preferably 100%, of the circumference of the generally circular main region of the stabilization assembly is in contact with a circumference inside the pulmonary vein or other tubular region.

If the stabilization assembly includes a series of ring electrodes mounted about the generally circular main region, the electrical activity in the pulmonary vein can be mapped before, after and/or during the ablation procedure. The circular arrangement of the electrodes permits measurement of the electrical activity at that circumference of the pulmonary vein so that ectopic beats between the electrodes can be identified. The size of the generally circular main region permits measurement of electrical activity along a diameter of a pulmonary vein or other tubular structure of or near the heart because the circular main region has a diameter generally corresponding to that of a pulmonary vein or the coronary sinus.

Once the ablation assembly is properly positioned at a desired location within the pulmonary vein or vein ostium, the pressurized fluid source inflates the balloon to engage the lumenal surface of the pulmonary vein ostium. Once properly positioned, the ultrasonic driver is energized to drive the transducer. Driving the ultrasonic transducer at 20 acoustical watts at an operating frequency of 7 megahertz can form a sufficiently sized lesion circumferentially about the pulmonary vein ostium in a relatively short period of time (e.g., 1 to 4 minutes or less).

The control level of energy can be delivered, then tested for lesion formation with a test stimulus in the pulmonary vein. A preferred method for determining whether the ablation created sufficient entrance and exit block is to pace with a catheter in the coronary sinus and use electrodes on the stabilization assembly to confirm no capture. Alternatively, one or more stabilization assembly electrodes can be used for pacing to confirm that the wavefront cannot pass to a second catheter outside the pulmonary vein, such as in the coronary sinus or left atrium. Other suitable techniques would be known to one skilled in the art. The circumferential ablation assembly may also include feedback control using, for example, one or more thermocouples provided on or around the ablation assembly. Monitoring temperature at this location provides indicia for the progression of the lesion. This feedback feature may be used in addition to or in the alternative to the multi-step procedure described above. Therefore, the procedure may involve ablation at a first energy level in time, then a check for the effective conductive block provided by the resulting lesion, and then subsequent ablations and testing until a complete conductive block is formed.

Figure 8A:
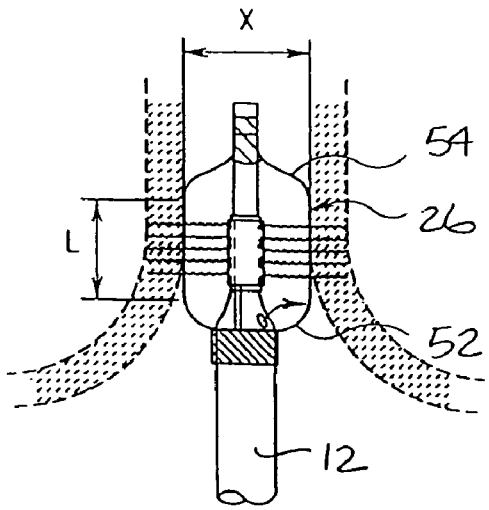
FIG. 8A is a perspective view of the distal end portion of an alternative embodiment of a circumferential ablation catheter during one mode of use in forming a circumferential conduction block in a pulmonary vein in the region of its ostium along a left atrial wall (shown in cross-section in shadow).
Figure 8B:
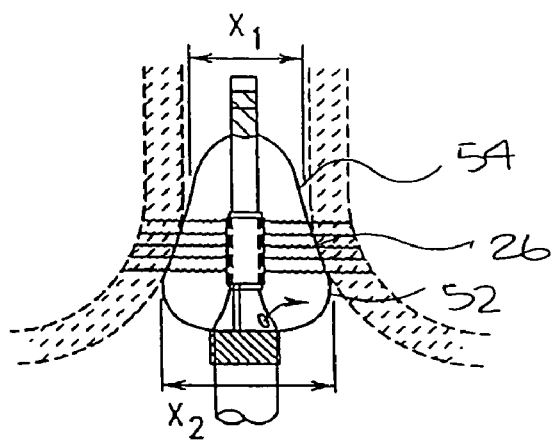
FIG. 8B is a perspective view of the distal end portion of an another alternative embodiment of a circumferential ablation catheter wherein the balloon has a tapered outer diameter.
Figure 8C:
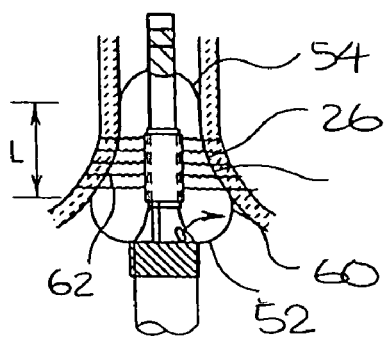
FIG. 8C is a perspective view of the distal end portion of an another alternative embodiment of a circumferential ablation catheter wherein the balloon has a "pear"-shaped outer diameter with a contoured surface along a taper which is adapted to seat in the ostium of a pulmonary vein.

FIGS. 8A to 8C show various alternative embodiments of the present invention for the purpose of illustrating the relationship between the ultrasound transducer 28 and balloon 26 of the present invention. Specifically, FIG. 8A shows the balloon 26 having a "straight" configuration with a working length D and a relatively constant diameter X between proximal and distal neck regions 52 and 54. As is shown in FIG. 8A, this variation is believed to be particularly well adapted for use in forming a circumferential conduction block along a circumferential path of tissue that circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon 26.

The balloon 26 depicted in FIG. 8A is also concentrically positioned relative to the longitudinal axis of the catheter body 12. It is understood, however, that the balloon 26 can be asymmetrically positioned relative to the catheter body 12, and that the ablation device can include more than one balloon.

FIG. 8B shows another ablation assembly 14 according to the invention, although this assembly includes a balloon 26 that has a tapered outer diameter from a proximal outer diameter $X_1$ to a smaller distal outer diameter $X_2$. (Like reference numerals are used in each of these embodiments in order to identify generally common elements between the embodiments.) This tapered shape is believed to conform well to other tapering regions of space, and may also be particularly beneficial for use in engaging and ablating circumferential paths of tissue along a pulmonary vein ostium.

Figure 8D:
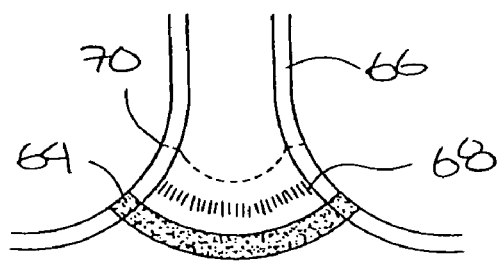
FIG. 8D is a cross-sectional view of one circumferential conduction block that can be formed by use of a circumferential ablation catheter such as that shown in FIG. 8C.

FIG. 8C shows a shape for the balloon 26 similar to that illustrated in FIG. 8B, except that the balloon in the FIG. 8C embodiment further includes primary region 50 with a bulbous proximal end 60. The bulbous proximal end 60 of the primary region 50 gives the balloon 26 a "pear" shape. More specifically, a contoured surface 62 is positioned between the proximal neck region 52 and the smaller distal neck region 54 of balloon 26. As is suggested by FIG. 8C, this pear-shaped embodiment is believed to be beneficial for forming the circumferential conduction block along a circumferential path of atrial wall tissue which surrounds and perhaps includes the pulmonary vein ostium. For example, the device shown in FIG. 8C is believed to be suited to form a circumferential lesion 64, as shown in FIG. 8D. The circumferential lesion 64 electrically isolates the respective pulmonary vein 66 from a substantial portion of the left atrial wall. The device shown in FIG. 8C is also believed to be suited to form an elongate lesion that extends along a substantial portion of the pulmonary vein ostium 68, e.g., between the proximal edge of the illustrated lesion 64 and the dashed line 70 that schematically marks a distal edge of such an exemplary elongate lesion.

As mentioned above, the transducer 28 can be formed of an array of multiple transducer elements that are arranged coaxially in series. The transducer can also be formed to have a plurality of longitudinal sectors. These modes of the transducer have particular utility in connection with the tapering balloon designs illustrated in FIGS. 8B and 8C. In these embodiments, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer is operating in an attenuating fluid, then the desired power level may need to account for the attenuation caused by the fluid. The region of smaller balloon diameter near the distal end thus requires less transducer power output than the region of larger balloon diameter near the proximal end.

The circumferential ablation device can also include additional mechanisms to control the depth of heating. For instance, the catheter body 12 can include an additional lumen (not shown) that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon 26 can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that fluids such as vegetable oil, silicone oil and the like are suitable for this application.

Uniform heating can also be enhanced by rotating the transducer 28 within the balloon 26. For this purpose, the transducer 28 may be mounted on a torquible member (not shown) that is movably engaged within a lumen of the catheter body 12.

Figure 9A:
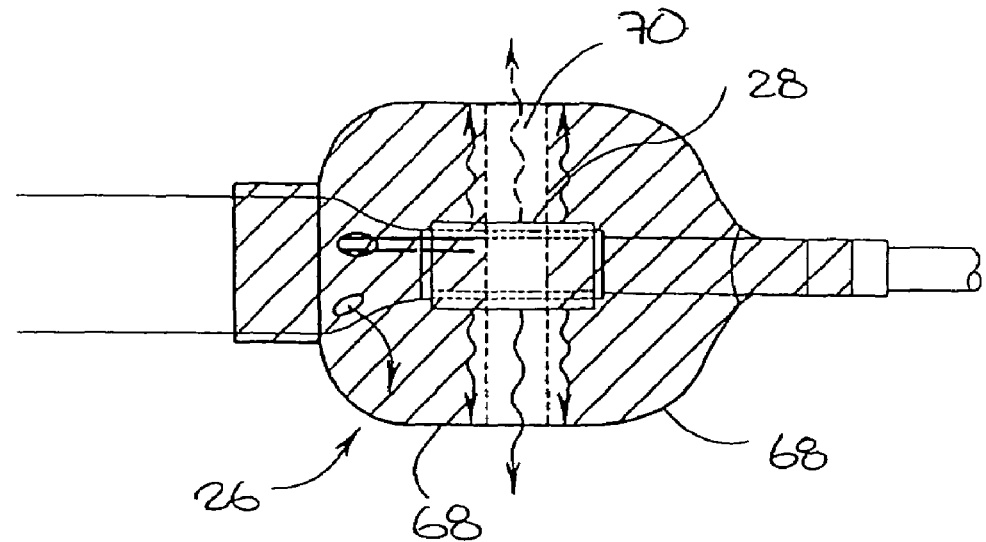
FIG. 9A is a cross-sectional view of the distal end portion of another embodiment of a circumferential ablation catheter according to the present invention, wherein an outer shield or filter is provided along the balloon's outer surface in order to form a predetermined shape for the circumferential ablation element created by sonic transmissions from the inner ultrasound transducer.

Another aspect of the balloon-transducer relationship of the present embodiment is illustrated by reference to FIGS. 9A-B. In this embodiment, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 8A-C). More particularly, FIG. 9A shows the balloon 26 to include a filter 68 that has a predetermined pattern along the balloon surface and that is adapted to shield tissue from the ultrasound signal, for example, by either absorbing or reflecting the ultrasound signal. In the embodiment shown in FIG. 9A, the filter 68 is patterned so that the energy band that is passed through the wall of the balloon 26 is substantially more narrow than the band that emits from the transducer 28 inside the balloon. The filter 68 can be constructed, for example, by coating the balloon 26 with an ultrasonically reflective material, such as a metal, or with an ultrasonically absorbent material, such as a polyurethane elastomer. Alternatively, the filter 68 can be formed by varying the thickness of the wall of the balloon 26 such that a circumferential band 70, which is narrow in the longitudinal direction compared to the length of the balloon, is also thinner (in a radial direction) than the surrounding regions, thereby preferentially allowing signals to pass through the band. Thicker balloon walls on either side of the circumferential band 70 inhibit propagation of the ultrasonic energy through the balloon at these locations.

For various reasons, the "narrow pass filter" embodiment of FIG. 9A may be particularly well-suited for use in forming circumferential conduction blocks in left atrial wall and pulmonary vein tissues. It is believed that the efficiency of ultrasound transmission from a piezoelectric transducer is limited by the length of the transducer, which limitations are further believed to be a function of the wavelength of the emitted signal. Thus, for some applications a transducer may be required to be longer than the length that is desired for the lesion to be formed. Many procedures for forming conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length that is much longer and may create lesions that are much wider than is functionally required for the block. A "narrow pass" filter along the balloon provides one solution to such competing interests.

Figure 9B:
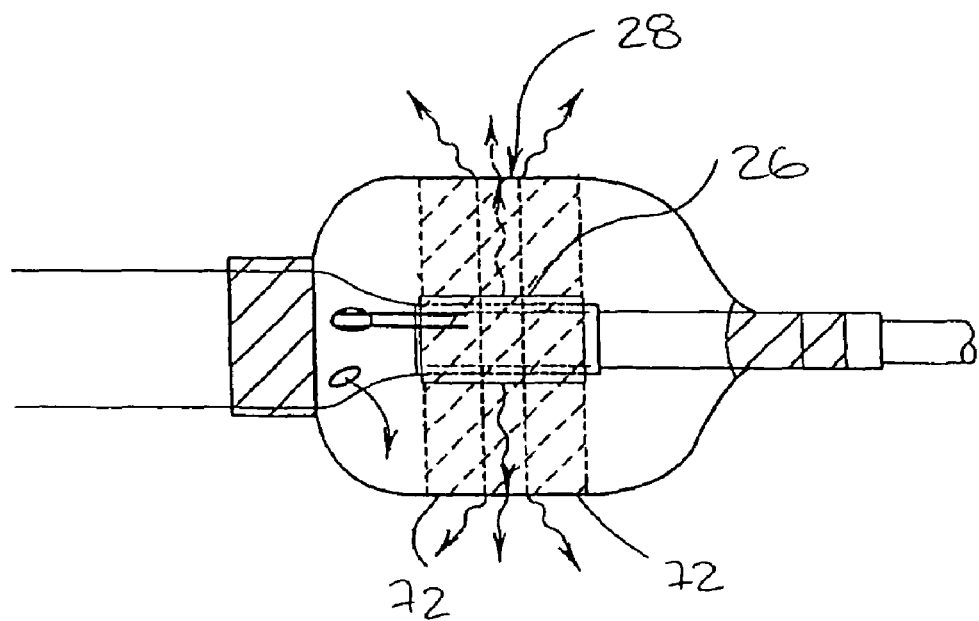
FIG. 9B is a cross-sectional view of the distal end portion of another embodiment of a circumferential ablation catheter according to the present invention that includes a heat sink as an equatorial band within the circumferential path of energy emission from an inner ultrasound transducer.

FIG. 9B shows another variation of the balloon-transducer relationship in an ultrasound ablation assembly according to the present invention. Unlike the variation shown in FIG. 9A, the embodiment of FIG. 9B has an ultrasonically absorbent band 72 along the balloon 26 and directly in the central region of the emitted energy signal from the transducer 28. According to this embodiment, the ultrasonically absorbent band 72 is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, the ultrasonically absorbent band 72 may operate as an energy sink as an aid to control the extent of ablation to a less traumatic and invasive level than would be reached by allowing the raw ultrasound energy to couple directly to the tissue. In other words, by heating the absorbent band 72, the signal is diminished to a level that might have a more controlled depth of tissue ablation. The absorbent band 72 may therefore also have a width that is more commensurate with the length of the transducer, as is shown in an alternative mode in shadow.

In each of the above-described embodiments, the ultrasonic transducer 28 has an annular shape so as to emit ultrasonic energy around the entire circumference of the balloon 26. The present circumferential ablation device, however, can emit a collimated beam of ultrasonic energy in a specific angular exposure. For instance, the transducer can be configured to have only a single active sector (e.g., 180 degree exposure). The transducer 28 also have a planar shape. By rotating the catheter body 12, the transducer 28 can be swept through 360 degrees in order to form a circumferential ablation. For this purpose, the transducer 28 may be mounted on a torquible member, in the manner described above.

Figure 10:
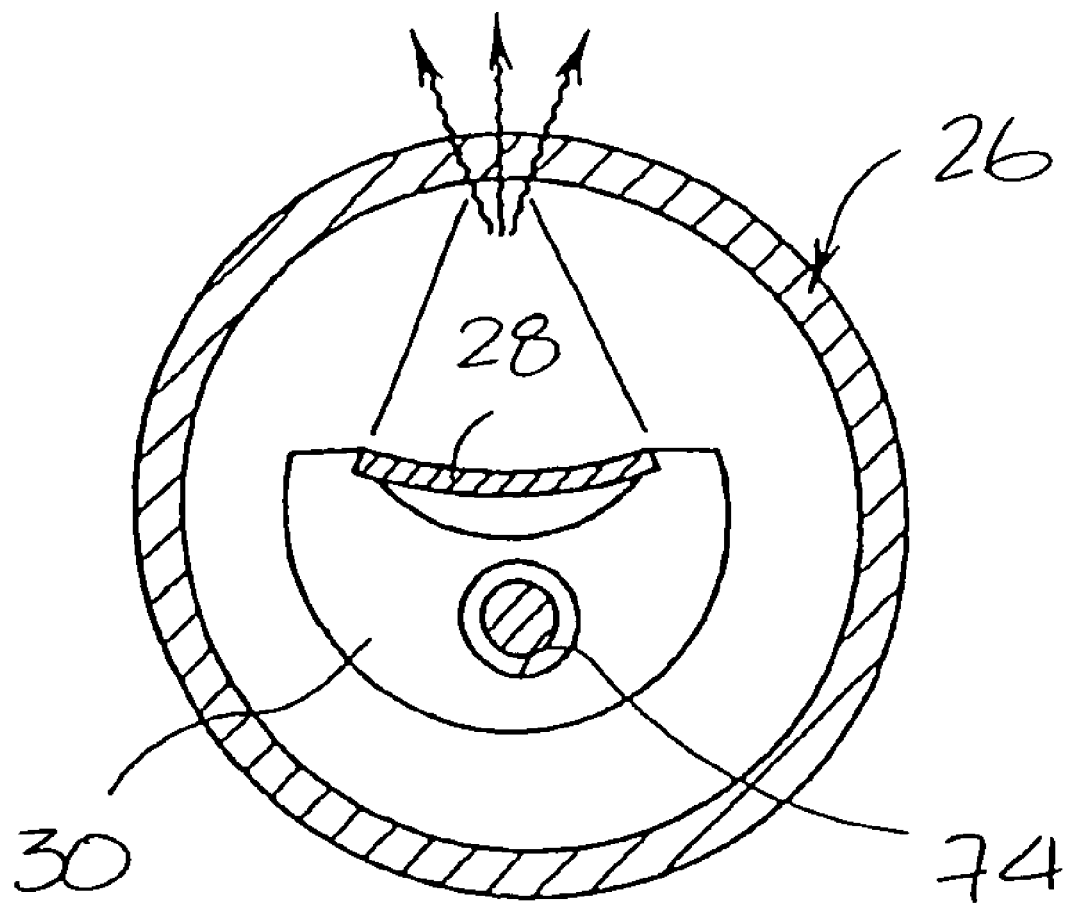
FIG. 10 is a transverse cross-sectional view of a further alternative embodiment of a circumferential ablation catheter according to the present invention showing the ablation element to include a single curvilinear section that is mounted so as to position its concave surface facing in a radially outward direction.

FIG. 10 illustrates another type of ultrasonic transducer 28 that can be mounted to a torquible member 74 within the balloon 26. The transducer 28 is formed by curvilinear section and is mounted on the inner support member 30 with its concave surface facing in a radially outward direction. The inner support member 30 preferably is formed with a recess that substantially matches a portion of the concave surface of the transducer 28. The inner support member 30 also includes longitudinal ridges on the edges of the recess that support the transducer 28 above the inner support member such that an air gap is formed between the transducer and the inner support member. In this manner, the transducer is "air-backed." This spaced is sealed and closed in the manner generally described above. The inverted transducer section produces a highly directional beam pattern. By sweeping the transducer through 360 degrees of rotation, as described above, a circumferential lesion can be formed while using less power than would be required with a planar or tubular transducer.

The circumferential ablation element has been described primarily as an annular ultrasonic transducer. However, other circumferential ablation elements can be used in connection with the invention, such as those described in U.S. Pat. No. 6,117,101, the entire disclosure of which is incorporated herein by reference.

The preceding description has been presented with reference to presently preferred embodiments of the invention. Workers skilled in the art and technology to which this invention pertains will appreciate that alterations and changes in the described structures and methods may be practiced without meaningfully departing from the principal, spirit and scope of this invention.

Accordingly, the foregoing description should not be read as pertaining only to the precise structures and methods described and illustrated in the accompanying drawings, but rather should be read consistent with and as support to the following claims which are to have their fullest and fair scope.

The invention claimed is:

1. A method for treating atrial arrhythmia by ablating a substantial portion of a circumferential region of tissue in a tubular region of or near the heart of a patient, comprising:
   providing a circumferential ablation catheter comprising:
      an elongated tubular catheter body having an outer wall, proximal and distal ends, and at least one lumen extending therethrough;
      an ablation assembly mounted at the distal end of the catheter body, the ablation assembly comprising:
         a circumferential ablation element mounted on the distal end of the catheter body; and an inflatable balloon provided in surrounding relation to the circumferential ablation element that is adjustable between a radially collapsed position and a radially expanded position, the inflation balloon contacting a plurality of locations about an inner circumferential region of a generally tubular region of or near the heart; and a stabilization assembly mounted on the catheter distal to the ablation assembly, the stabilization assembly contacting a different plurality of locations about the inner circumferential region of the generally tubular region of or near the heart when the inflatable balloon is in the radially expanded position;

wherein the stabilization assembly comprises a tubular structure comprising a generally circular main region that is generally transverse to the catheter body and a generally straight distal region;

introducing into a patient the catheter, wherein the circumferential ablation element comprises an ultrasound ablation element coupled to an acoustic energy driver, so that the stabilization assembly is within the tubular region and in contact with the different plurality of locations about the inner circumferential region of the tubular region;

contacting the substantial portion of the circumferential region of tissue with at least a portion of the inflatable balloon, such that the ultrasound ablation element is positioned to deliver a substantially circumferential pattern of ultrasound energy through the inflatable balloon to the substantial portion of the circumferential region of tissue; and actuating the acoustic energy driver to ablatively couple the ultrasound ablation element to the substantial portion of the circumferential region of tissue via the inflatable balloon.

2. A method according to claim 1, wherein contacting at least the substantial portion of the circumferential region of tissue comprises expanding the inflatable balloon to radially engage the substantial portion of the circumferential region of tissue.

3. A method according to claim 2, wherein expanding the inflatable balloon comprises introducing an ultrasonically transparent inflation fluid to an inner region of the inflatable balloon.

4. A method according to claim 3, wherein the ultrasonically transparent inflation fluid comprises a radiopaque dye.

5. A method according to claim 2, wherein expanding the inflatable balloon comprises increasing the diameter of the inflatable balloon to at least about 1 cm.

6. A method according to claim 1, further comprising ablatively coupling the ultrasound ablation element to the substantial portion of the circumferential region of tissue at a location where cardiac tissue extends along the pulmonary vein.

7. A method according to claim 1, further comprising ablatively coupling the ultrasound ablation element to the substantial portion of the circumferential region of tissue at a location where cardiac tissue extends along an ostium of the pulmonary vein.

8. A method according to claim 1, further comprising ablatively coupling the ultrasound ablation element to the substantial portion of the circumferential region of tissue at a location along the atrial wall and surrounding an ostium of the pulmonary vein.

9. A method according to claim 1, further comprising actuating the ultrasound ablation element to emit the substantially circumferential pattern of ultrasound energy at a frequency ranging from about 5 MHz to about 20 MHz.

10. A method according to claim 1, wherein the entire circumferential region of tissue is ablatively coupled to the ultrasound ablation element.

11. A method for treating atrial arrhythmia by ablating a substantial portion of a circumferential region of tissue in a tubular region of or near the heart of a patient, comprising:

providing a circumferential ablation catheter comprising:

an elongated tubular catheter body having an outer wall, proximal and distal ends, and at least one lumen extending therethrough;

an ablation assembly mounted at the distal end of the catheter body, the ablation assembly comprising:

a circumferential ablation element mounted on the distal end of the catheter body; and an inflatable balloon provided in surrounding relation to the circumferential ablation element that is adjustable between a radially collapsed position and a radially expanded position; and a stabilization assembly mounted on the catheter distal to the ablation assembly, the stabilization assembly being capable of contacting a plurality of points about an inner circumference of a generally tubular region of or near the heart;

wherein the stabilization assembly comprises a tubular structure comprising a generally circular main region that is generally transverse to the catheter body and a generally straight distal region; and wherein the stabilization assembly comprises a plurality of electrodes carried by the generally circular main region, wherein the electrodes are generally evenly spaced about the entire circumference of the generally circular main region such that, in use, when the stabilization assembly is positioned in a tubular region of or near the heart, with the outer circumference of the generally circular main region in contact with the inner circumference of the tubular region, the electrodes can be used to map the inner circumference of the tubular region;

introducing into a patient the catheter, wherein the circumferential ablation element comprises an ultrasound ablation element coupled to an acoustic energy driver, so that the stabilization assembly is within the tubular region and in contact with the different plurality of locations about the inner circumferential region of the tubular region;

contacting the substantial portion of the circumferential region of tissue with at least a portion of the inflatable balloon, such that the ultrasound ablation element is positioned to deliver a substantially circumferential pattern of ultrasound energy through the inflatable balloon to the substantial portion of the circumferential region of tissue; and actuating the acoustic energy driver to ablatively couple the ultrasound ablation element to the substantial portion of the circumferential region of tissue via the inflatable balloon.

12. A method according to claim 11, wherein contacting at least the substantial portion of the circumferential region of tissue comprises expanding the inflatable balloon to radially engage the substantial portion of the circumferential region of tissue.

13. A method according to claim 12, wherein expanding the inflatable balloon comprises introducing an ultrasonically transparent inflation fluid to an inner region of the inflatable balloon.

14. A method according to claim 13, wherein the ultrasonically transparent inflation fluid comprises a radiopaque dye.

15. A method according to claim 12, wherein expanding the inflatable balloon comprises increasing the diameter of the inflatable balloon to at least about 1 cm.

16. A method according to claim 11, further comprising ablatively coupling the ultrasound ablation element to the substantial portion of the circumferential region of tissue at a location where cardiac tissue extends along the pulmonary vein.

17. A method according to claim 11, further comprising ablatively coupling the ultrasound ablation element to the substantial portion of the circumferential region of tissue at a location where cardiac tissue extends along an ostium of the pulmonary vein.

18. A method according to claim 11, further comprising ablatively coupling the ultrasound ablation element to the substantial portion of the circumferential region of tissue at a location along the atrial wall and surrounding an ostium of the pulmonary vein.

19. A method according to claim 11, further comprising actuating the ultrasound ablation element to emit the substantially circumferential pattern of ultrasound energy at a frequency ranging from about 5 MHz to about 20 MHz.

20. A method according to claim 11, wherein the entire circumferential region of tissue is ablatively coupled to the ultrasound ablation element.

21. A method for treating atrial arrhythmia by ablating a substantial portion of a circumferential region of tissue in a tubular region of or near the heart of a patient, comprising:
providing a circumferential ablation catheter comprising:
an elongated tubular catheter body having an outer wall, proximal and distal ends, and at least one lumen extending therethrough;
an ablation assembly mounted at the distal end of the catheter body, the ablation assembly comprising:
a circumferential ablation element mounted on the distal end of the catheter body; and
an inflatable balloon provided in surrounding relation to the circumferential ablation element that is adjustable between a radially collapsed position and a radially expanded position; and
a stabilization assembly mounted on the catheter distal to the ablation assembly, the stabilization assembly being capable of contacting a plurality of points about an inner circumference of a generally tubular region of or near the heart;
wherein the stabilization assembly comprises a tubular structure comprising a generally circular main region that is generally transverse to the catheter body and a generally straight distal region;
wherein the stabilization assembly carries a plurality of ring electrodes mounted around the generally circular main region; and
wherein the number of electrodes along the generally circular main region ranges from about six to about twenty;
introducing into a patient the catheter, wherein the circumferential ablation element comprises an ultrasound ablation element coupled to an acoustic energy driver, so that the stabilization assembly is within the tubular region and in contact with the different plurality of locations about the inner circumferential region of the tubular region;
contacting the substantial portion of the circumferential region of tissue with at least a portion of the inflatable balloon, such that the ultrasound ablation element is positioned to deliver a substantially circumferential pattern of ultrasound energy through the inflatable balloon to the substantial portion of the circumferential region of tissue; and
actuating the acoustic energy driver to ablatively couple the ultrasound ablation element to the substantial portion of the circumferential region of tissue via the inflatable balloon.

22. A method according to claim 21, wherein contacting at least the substantial portion of the circumferential region of tissue comprises expanding the inflatable balloon to radially engage the substantial portion of the circumferential region of tissue.

23. A method according to claim 22, wherein expanding the inflatable balloon comprises introducing an ultrasonically transparent inflation fluid to an inner region of the inflatable balloon.

24. A method according to claim 23, wherein the ultrasonically transparent inflation fluid comprises a radiopaque dye.

25. A method according to claim 22, wherein expanding the inflatable balloon comprises increasing the diameter of the inflatable balloon to at least about 1 cm.

26. A method according to claim 21, further comprising ablatively coupling the ultrasound ablation element to the substantial portion of the circumferential region of tissue at a location where cardiac tissue extends along the pulmonary vein.

27. A method according to claim 21, further comprising ablatively coupling the ultrasound ablation element to the substantial portion of the circumferential region of tissue at a location where cardiac tissue extends along an ostium of the pulmonary vein.

28. A method according to claim 21, further comprising ablatively coupling the ultrasound ablation element to the substantial portion of the circumferential region of tissue at a location along the atrial wall and surrounding an ostium of the pulmonary vein.

29. A method according to claim 21, further comprising actuating the ultrasound ablation element to emit the substantially circumferential pattern of ultrasound energy at a frequency ranging from about 5 MHz to about 20 MHz.

30. A method according to claim 21, wherein the entire circumferential region of tissue is ablatively coupled to the ultrasound ablation element.

31. A method for treating atrial arrhythmia by ablating a substantial portion of a circumferential region of tissue in a tubular region of or near the heart of a patient, comprising:
providing a circumferential ablation catheter comprising:
an elongated tubular catheter body having an outer wall, proximal and distal ends, and at least one lumen extending therethrough;
an ablation assembly mounted at the distal end of the catheter body, the ablation assembly comprising:
a circumferential ablation element mounted on the distal end of the catheter body; and
an inflatable balloon provided in surrounding relation to the circumferential ablation element that is adjustable between a radially collapsed position and a radially expanded position; and
a stabilization assembly mounted on the catheter distal to the ablation assembly, the stabilization assembly being capable of contacting a plurality of points about an inner circumference of a generally tubular region of or near the heart;
wherein the stabilization assembly comprises a tubular structure comprising a generally circular main region that is generally transverse to the catheter body and a generally straight distal region;

wherein the stabilization assembly carries a plurality of ring electrodes mounted around the generally circular main region; and wherein the number of electrodes along the generally circular main region ranges from about eight to about twelve;

introducing into a patient the catheter, wherein the circumferential ablation element comprises an ultrasound ablation element coupled to an acoustic energy driver, so that the stabilization assembly is within the tubular region and in contact with the different plurality of locations about the inner circumferential region of the tubular region;

contacting the substantial portion of the circumferential region of tissue with at least a portion of the inflatable balloon, such that the ultrasound ablation element is positioned to deliver a substantially circumferential pattern of ultrasound energy through the inflatable balloon to the substantial portion of the circumferential region of tissue; and actuating the acoustic energy driver to ablatively couple the ultrasound ablation element to the substantial portion of the circumferential region of tissue via the inflatable balloon.

32. A method according to claim 31, wherein contacting at least the substantial portion of the circumferential region of tissue comprises expanding the inflatable balloon to radially engage the substantial portion of the circumferential region of tissue.

33. A method according to claim 32, wherein expanding the inflatable balloon comprises introducing an ultrasonically transparent inflation fluid to an inner region of the inflatable balloon.

34. A method according to claim 33, wherein the ultrasonically transparent inflation fluid comprises a radiopaque dye.

35. A method according to claim 32, wherein expanding the inflatable balloon comprises increasing the diameter of the inflatable balloon to at least about 1 cm.

36. A method according to claim 31, further comprising ablatively coupling the ultrasound ablation element to the substantial portion of the circumferential region of tissue at a location where cardiac tissue extends along the pulmonary vein.

37. A method according to claim 31, further comprising ablatively coupling the ultrasound ablation element to the substantial portion of the circumferential region of tissue at a location where cardiac tissue extends along an ostium of the pulmonary vein.

38. A method according to claim 31, further comprising ablatively coupling the ultrasound ablation element to the substantial portion of the circumferential region of tissue at a location along the atrial wall and surrounding an ostium of the pulmonary vein.

39. A method according to claim 31, further comprising actuating the ultrasound ablation element to emit the substantially circumferential pattern of ultrasound energy at a frequency ranging from about 5 MHz to about 20 MHz.

40. A method according to claim 31, wherein the entire circumferential region of tissue is ablatively coupled to the ultrasound ablation element.

* * * * *